US009096541B2

(12) United States Patent
Tang et al.

(10) Patent No.: US 9,096,541 B2
(45) Date of Patent: Aug. 4, 2015

(54) INHIBITION OF MEMAPSIN 1 CLEAVAGE IN THE TREATMENT OF DIABETES

(71) Applicants: Jordan Tang, Oklahoma City, OK (US); Xiangping Huang, Oklahoma City, OK (US); Deborah Downs, Oklahoma City, OK (US); Arun K. Ghosh, West Lafayette, IN (US)

(72) Inventors: Jordan Tang, Oklahoma City, OK (US); Xiangping Huang, Oklahoma City, OK (US); Deborah Downs, Oklahoma City, OK (US); Arun K. Ghosh, West Lafayette, IN (US)

(73) Assignees: Oklahoma Medical Research Foundation, Oklahoma City, OK (US); Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 13/794,031

(22) Filed: Mar. 11, 2013

(65) Prior Publication Data

US 2013/0261052 A1 Oct. 3, 2013

Related U.S. Application Data

(60) Provisional application No. 61/617,493, filed on Mar. 29, 2012.

(51) Int. Cl.
| | |
|---|---|
| *A61K 31/166* | (2006.01) |
| *A61K 31/4965* | (2006.01) |
| *A61K 38/05* | (2006.01) |
| *C07D 239/84* | (2006.01) |
| *C07D 403/12* | (2006.01) |
| *C07D 417/12* | (2006.01) |
| *C07D 413/12* | (2006.01) |
| *C07D 513/04* | (2006.01) |
| *C07D 241/04* | (2006.01) |
| *C07K 5/02* | (2006.01) |
| *C07C 311/08* | (2006.01) |
| *A61K 31/495* | (2006.01) |
| *A61K 31/18* | (2006.01) |

(52) U.S. Cl.
CPC ............ *C07D 239/84* (2013.01); *A61K 31/166* (2013.01); *A61K 31/18* (2013.01); *A61K 31/495* (2013.01); *A61K 38/05* (2013.01); *C07C 311/08* (2013.01); *C07D 241/04* (2013.01); *C07D 403/12* (2013.01); *C07D 413/12* (2013.01); *C07D 417/12* (2013.01); *C07D 513/04* (2013.01); *C07K 5/0207* (2013.01)

(58) Field of Classification Search
None
See application file for complete search history.

(56) References Cited

U.S. PATENT DOCUMENTS

| | | | |
|---|---|---|---|
| 2006/0079686 A1 | 4/2006 | Baxter et al. | |
| 2006/0178383 A1* | 8/2006 | Bischoff et al. | 514/266.23 |
| 2006/0229302 A1 | 10/2006 | Demont et al. | |
| 2006/0234944 A1* | 10/2006 | Ghosh et al. | 514/17 |
| 2008/0207527 A1 | 8/2008 | Ghosh et al. | |
| 2010/0216800 A1 | 8/2010 | Rachman | |
| 2011/0195978 A1* | 8/2011 | Ghosh | 514/255.05 |
| 2012/0035195 A1* | 2/2012 | Banner et al. | 514/272 |
| 2012/0053200 A1 | 3/2012 | Mauser et al. | |
| 2014/0066488 A1* | 3/2014 | Tang et al. | 514/411 |

FOREIGN PATENT DOCUMENTS

WO WO/2011/029803 3/2011

OTHER PUBLICATIONS

Casas S, Casini P, Piquer S, Altirriba J, Soty M, Cadavez L, Gomis R, Novials A. (2010). "BACE2 plays a role in the insulin receptor trafficking in pancreatic β-cells." *Am J Physiol Endocrinol Metab.* 299: E1087-1095.
Esterházy, D., Stützer, I., Wang, H. et al. (2011). "Bace2 Is a Beta Cell-Enriched Protease that Regulates Pancreatic Beta Cell Function and Mass." *Cell Metab.* 14, 365-377.
Ghosh A. K., Bilcer G., Harwood C. et al. (2001) "Structure-based design: potent inhibitors of human brain memapsin 2 (b-secretase)." *J. Med. Chem.* 44, 2865-2868.
Ghosh A. K., Devasamudram T., Hong L., DeZutter C., Xu X., Weerasena V., Koelsch G., Bilcer G. and Tang J. (2005) "Structure based design of cycloamide-urethane-derived novel inhibitors of human brain memapsin 2 (b-secretase)." *Bioorg. Med. Chem. Lett.* 15, 15-20.
Ghosh A. K., Kumaragurubaran N., Hong L. et al. (2007) "Design, synthesis, and X-ray structure of potent memapsin 2 (beta-secretase) inhibitors with isophthalamide derivatives as the P2-P3-ligands." *J. Med. Chem.* 50, 2399-2407.
Ghosh A. K., Kumaragurubaran N., Hong L. et al. (2008) "Potent memapsin 2 (beta-secretase) inhibitors: Design, synthesis, protein-ligand X ray structure, and in vivo evaluation." *Bioorg. Med. Chem. Lett.* 18, 1031-1036.
Matera, Riccardo. "Design and synthesis of novel non peptidomimtic beta-secratase inhibitors in the treatment of Alzheimer's disease." Diss. University of Bologna, 2009. Print.
PCT International Search Report and Written Opinion issued in International Application No. (PCT/US13/30156), dated Mar. 11, 2013.

* cited by examiner

*Primary Examiner* — Jeffrey E Russel
(74) *Attorney, Agent, or Firm* — Parker Highlander PLLC

(57) ABSTRACT

Proteases such as memapsin-1 are import enzymes, playing roles in a variety of diseases including diabetes. The inventors have developed inhibitors of memapsin 1 and methods of use therefore in the treatment of disease.

18 Claims, 4 Drawing Sheets

INHIBITION OF MEMAPSIN 1 CLEAVAGE IN THE TREATMENT OF DIABETES

This application claims benefit of priority to U.S. Provisional Application Ser. No. 61/617,493, filed Mar. 29, 2012, the entire contents of which are hereby incorporated by reference.

This invention was made with government support under grant no. AG018933 awarded by the National Institutes of Health. The government has certain rights in the invention.

BACKGROUND OF THE INVENTION

I. Field of the Invention

The present invention relates generally to the fields of enzymology and biochemistry. More particularly, it concerns the inhibition of the memapsin 1 protease and the treatment of memapsin 1-related diseases, including diabetes.

II. Description of Related Art

At the turn of this century 171 million individuals were estimated to have diabetes in the world, and this is expected to increase to 366 million by 2030 (Wild et al., 2004). Currently, 25.8 million people in the United States have diabetes. Therefore, diabetes represents a major illness and development of new effective treatments is of great importance.

About 90% of diabetes cases are Type 2 diabetes which is characterized by hyperglycemia resulting from both the reduction of the pancreatic beta-cell functions and mass, which causes an insufficient insulin production, and an increase of insulin demand associated with insulin resistance (Kahn et al., 2009). Thus, clinical interventions to increase beta-cell functions and mass are attractive approaches for the treatment of Type 2 diabetes.

Tmem27, also called collectrin, is a 46 kDa type I transmembrane protein consisting an ectodomain, a transmembrane domain and an intracellular domain. Tmem27 is present in relatively large amount in the pancreatic beta cells (Akpinar et al., 2005) and has been shown to associate with beta cell functions and Type 2 diabetes (Altirriba et al., 2010). Genetic mutations of transcription factor Tcf1, which regulates Tmem27 expression, are known to cause a form of diabetes (Shih et al., 2001). Interestingly, overexpression of Tmem27 in pancreatic beta cells leads to increased beta-cell proliferation, cell mass increase (Akpinar et al., 2005), and improved glucose stimulated insulin secretion (Fukui et al., 2005).

The abundance of Tmem27 protein in beta cells is regulated by ectodomain cleavage, which leads to two cleavage products, a 25 kDa N-terminal fragment that is ultimately released into the extracellular space, and a 22 kDa C-terminal fragment anchored to the membrane and is rapidly degraded by gamma-secretase (Akpinar et al., 2005). The processing of Tmem27, which inactivates its activity, reduces the functions of Tmem27 and the inhibition of Tmem27 degradation results in up-regulating beta cell mass and functions. The protease that cleaves off the ectodomain of Tmem27 has only recently been identified to be memapsin 1, also known as BACE2 (Esterhazy et al., 2011). In this study, mice with functionally inactive memapsin 1 and insulin-resistant mice treated with a siRNA memapsin 1 inhibitor both displayed augmented beta cell mass and improved control of glucose homeostasis due to increased insulin levels. Interestingly, memapsin 1 is also involved in the trafficking of insulin receptor in the beta cells (Casas et al., 2010).

SUMMARY OF THE INVENTION

Thus, in accordance with the present invention, a method of inhibiting memapsin 1 activity comprising contacting a memapsin 1 enzyme with a compound having a formula selected from:

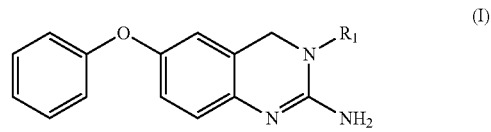
(I)

wherein $R_1$ is

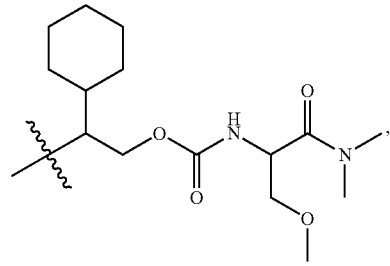

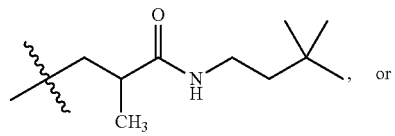
, or

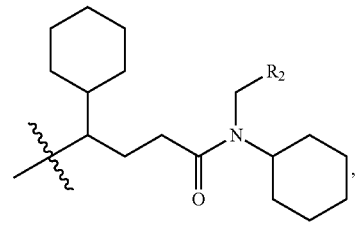
, wherein $R_2$ is heteroaryl$_{(C \leq 8)}$, heterocycloalkyl$_{(C \leq 8)}$, a substituted version of either of these groups, or

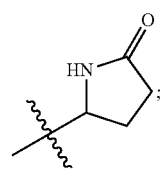
;

(IIa)

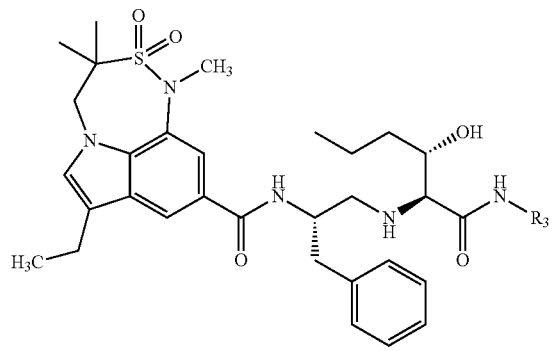

(IIb)

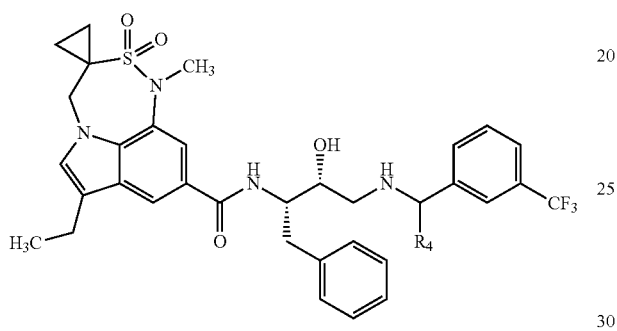

wherein R₃ is alkyl$_{(C \leq 8)}$ or a substituted version thereof;
wherein R₄ is hydrogen, alkyl$_{(C \leq 8)}$ or substituted alkyl$_{(C \leq 8)}$;

(III)

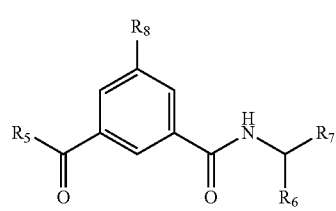

wherein: R₅ is

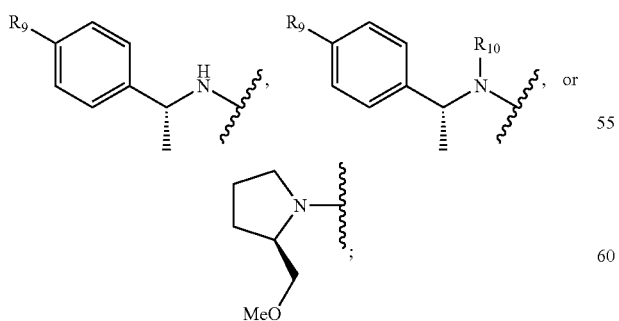

wherein: R₉ is hydrogen or halo; R₁₀ is alkyl$_{(C \leq 4)}$; R₆ is hydrogen, alkyl$_{(C \leq 8)}$, aralkyl$_{(C \leq 8)}$, or a substituted version of either of these groups; or a halogen; and R₇ is:

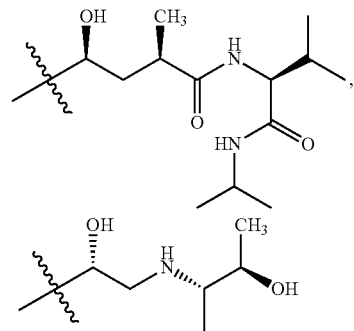

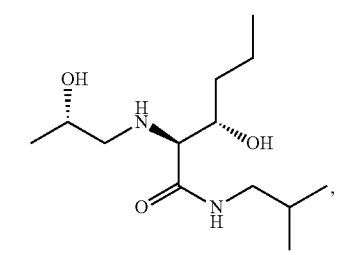

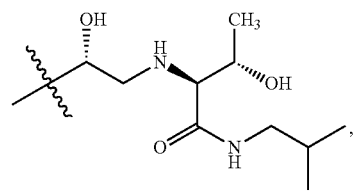

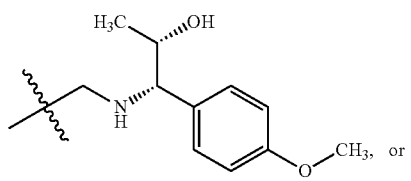

wherein R₈ is hydrogen, alkyl$_{(C \leq 8)}$, or

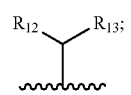

wherein: R₁₂ and R₁₃ are each independently hydrogen, alkyl$_{(C \leq 8)}$, or alkylsulfonyl$_{(C \leq 8)}$; and

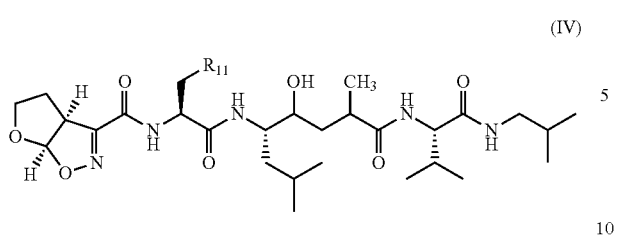

(IV)

wherein $R_{11}$ is alkylthio$_{(C \leq 8)}$, or alkylsulfonyl$_{(C \leq 8)}$, or a pharmaceutically acceptable salt or tautomer of any of the above formulas.

In some embodiments, the compound has formula I, wherein $R_1$ is:

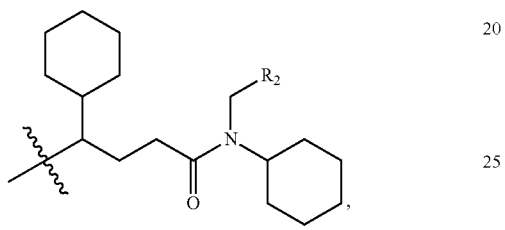

wherein $R_2$ is methylisoxazolyl or methylthiazolyl. In other embodiments, the compound has formula IIa, wherein $R_3$ is isopropyl or isobutyl. In other embodiments, the compound has formula IIb, wherein $R_4$ is hydrogen or methoxymethyl. In other embodiments, the compound has formula III, wherein the formula is:

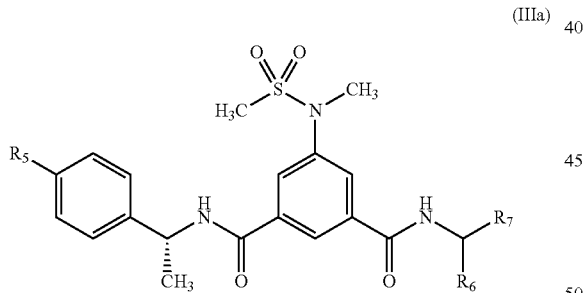

(IIIa)

wherein: $R_5$ is hydrogen or halo; $R_6$ is hydrogen, alkyl$_{(C \leq 8)}$, aralkyl$_{(C \leq 8)}$, or a substituted version of either of these groups; or a halogen; and $R_7$ is:

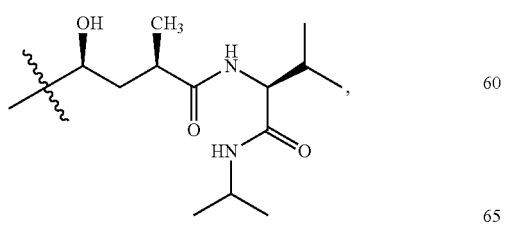

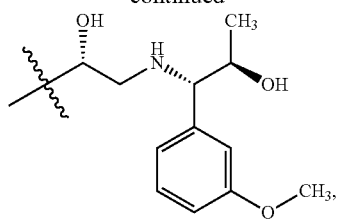

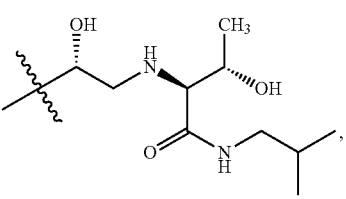

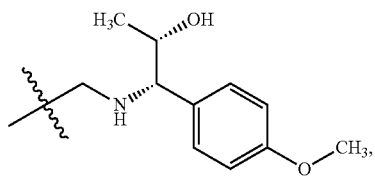

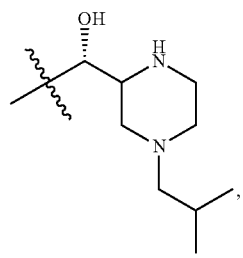

or a pharmaceutically acceptable salt or tautomer.

In some embodiments, the compound has formula III, wherein $R_5$ is

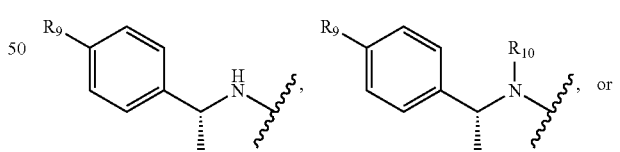

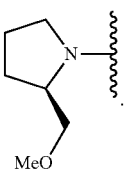

In some embodiments, $R_9$ is hydrogen. In other embodiments, $R_9$ is halo. In other embodiments, $R_{10}$ is alkyl$_{(C \leq 4)}$. In some embodiments, $R_{10}$ is methyl. In some embodiments, $R_6$ is benzyl or isobutyl. In some embodiments, the compound has formula III, wherein $R_7$ is:

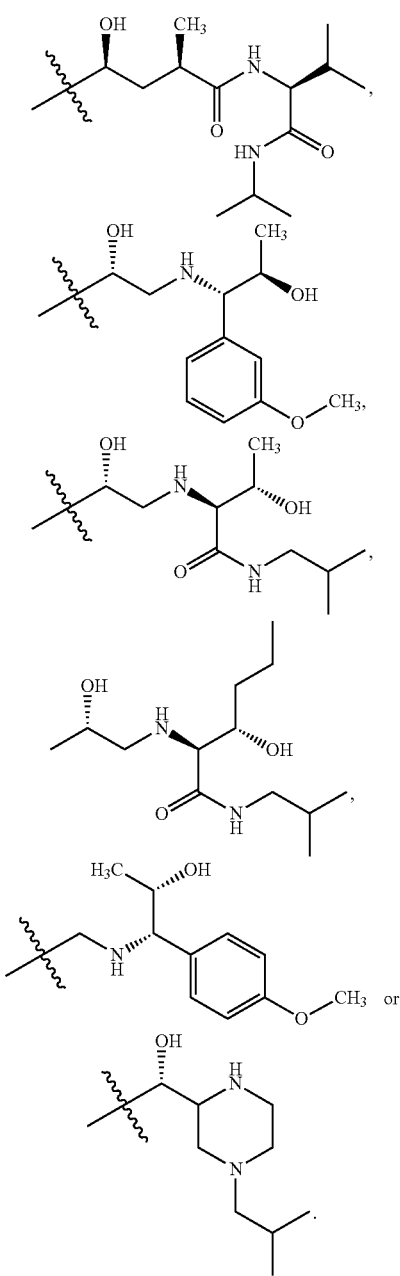

In some embodiments, $R_8$ is hydrogen. In other embodiments, the compound has formula III, wherein $R_8$ is alkyl$_{(C \leq 8)}$. In other embodiments, the compound has formula III, wherein $R_8$ is

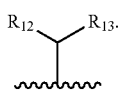

In some embodiments, $R_{12}$ is hydrogen. In some embodiments, $R_{12}$ is alkyl$_{(C \leq 8)}$. In some embodiments, $R_{12}$ is methyl. In other embodiments, $R_{12}$ is alkylsulfonyl$_{(C \leq 8)}$. In some embodiments, $R_{12}$ is methylsulfonyl. In other embodiments, $R_{13}$ is alkyl$_{(C \leq 8)}$. In some embodiments, $R_{13}$ is methyl. In other embodiments, $R_{13}$ is alkylsulfonyl$_{(C \leq 8)}$. In some embodiments, $R_{13}$ is methylsulfonyl. In some embodiments, the compound has formula III, wherein $R_9$ is hydrogen. In other embodiments, the compound has formula III, wherein $R_9$ is iodo.

In other embodiments, the compound has formula IV, wherein $R_{11}$ is —SCH$_3$ or —SO$_2$CH$_3$.

The invention also provides a method of treating a mammalian subject with type 2 diabetes comprising administering to said subject a compound having a formula selected from:

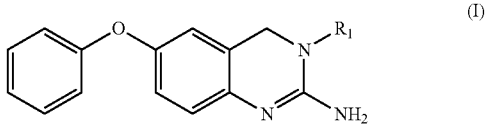

wherein $R_1$ is

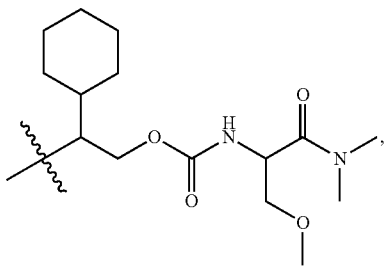

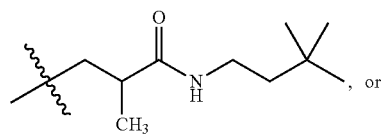

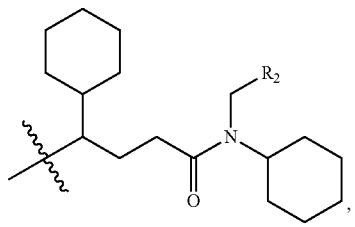

wherein $R_2$ is heteroaryl$_{(C \leq 8)}$, heterocycloalkyl$_{(C \leq 8)}$, a substituted version of either of these groups, or

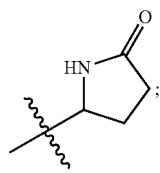

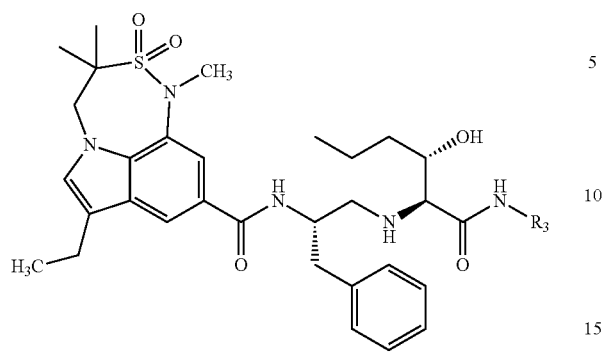

(IIa)

wherein R₃ is alkyl$_{(C≤8)}$, or a substituted version thereof;

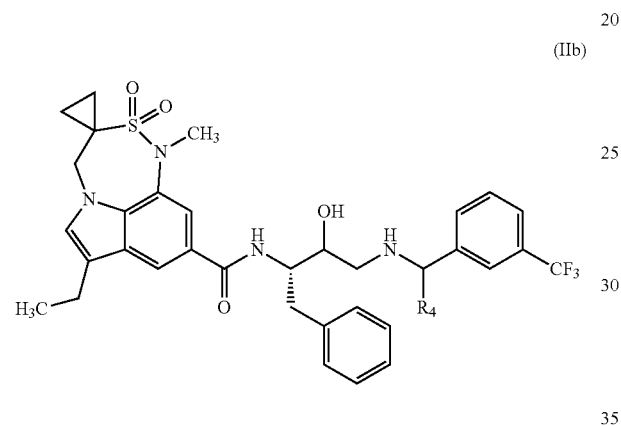

(IIb)

wherein R₄ is hydrogen, alkyl$_{(C≤8)}$ or substituted alkyl$_{(C≤8)}$;

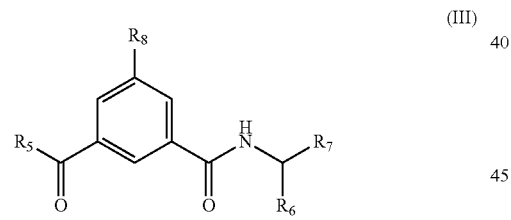

(III)

wherein: R₅ is

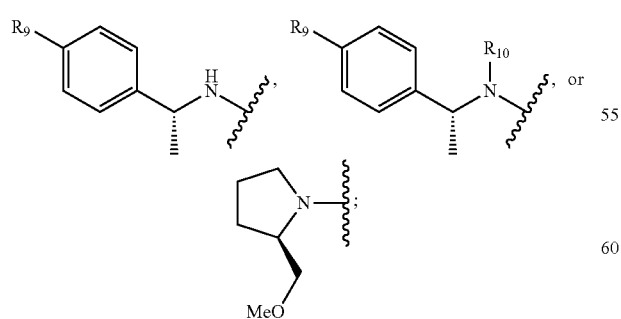

wherein: R₉ is hydrogen or halo; R₁₀ is alkyl$_{(C≤4)}$; R₆ is hydrogen, alkyl$_{(C≤8)}$, aralkyl$_{(C≤8)}$, or a substituted version of either of these groups; or a halogen; and R₇ is:

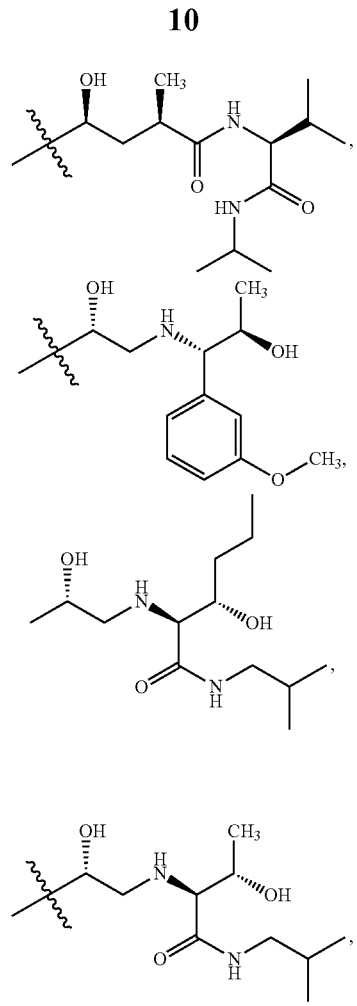

R₈ is hydrogen, alkyl$_{(C≤8)}$, or

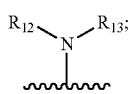

wherein: R₁₂ and R₁₃ are each independently hydrogen, alkyl$_{(C≤8)}$, or alkylsulfonyl$_{(C≤8)}$; and (IV)

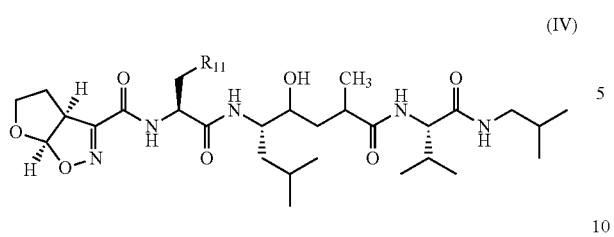

wherein $R_{11}$ is alkylthio$_{(C \leq 8)}$, or alkylsulfonyl$_{(C \leq 8)}$, or a pharmaceutically acceptable salt or tautomer of any of the above formulas.

In some embodiments, the compound has formula I, wherein $R_1$ is:

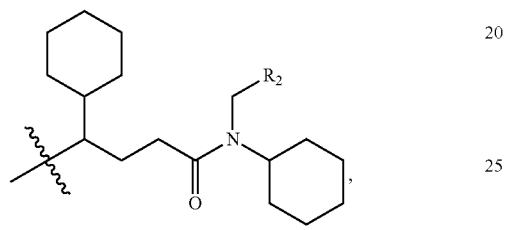

wherein $R_2$ is methylisoxazolyl or methylthiazolyl. In other embodiments, the compound has formula IIa, wherein $R_3$ is isopropyl or isobutyl. In other embodiments, the compound has formula IIb, wherein $R_4$ is hydrogen or methoxymethyl. In other embodiments, the compound has formula III, wherein the formula is:

(IIIa)

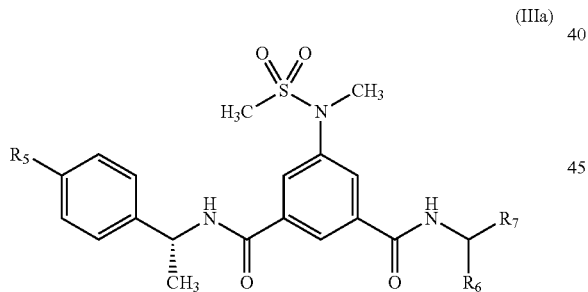

wherein: $R_5$ is hydrogen or halo; $R_6$ is hydrogen, alkyl$_{(C \leq 8)}$, aralkyl$_{(C \leq 8)}$, or a substituted version of either of these groups; or a halogen; and $R_7$ is:

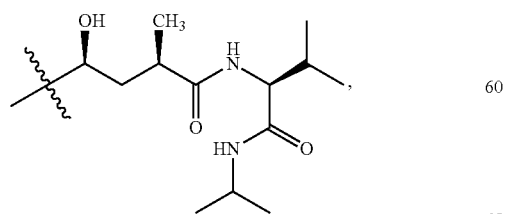

-continued

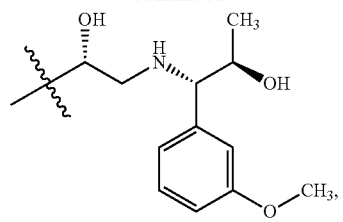

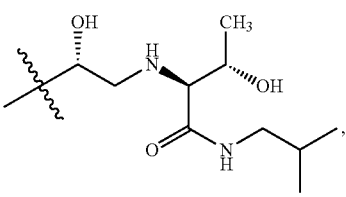

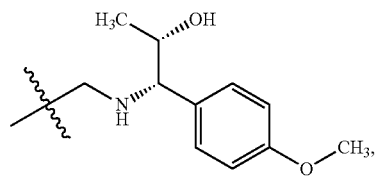

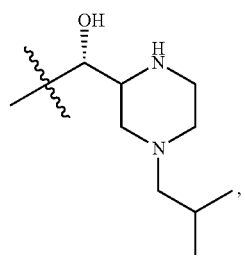

or a pharmaceutically acceptable salt or tautomer.

In some embodiments, the compound has formula III, wherein $R_5$ is

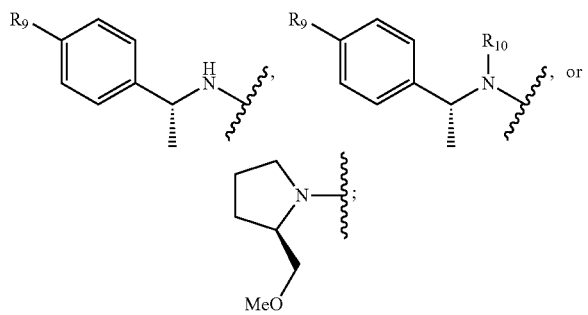

In some embodiments, $R_9$ is hydrogen. In other embodiments, $R_9$ is halo. In some embodiments, $R_{10}$ is alkyl$_{(C \leq 4)}$. In some embodiments, $R_{10}$ is methyl. In some embodiments, the compound has formula III, wherein $R_6$ is benzyl or isobutyl.

In some embodiments, the compound has formula III, wherein $R_7$ is:

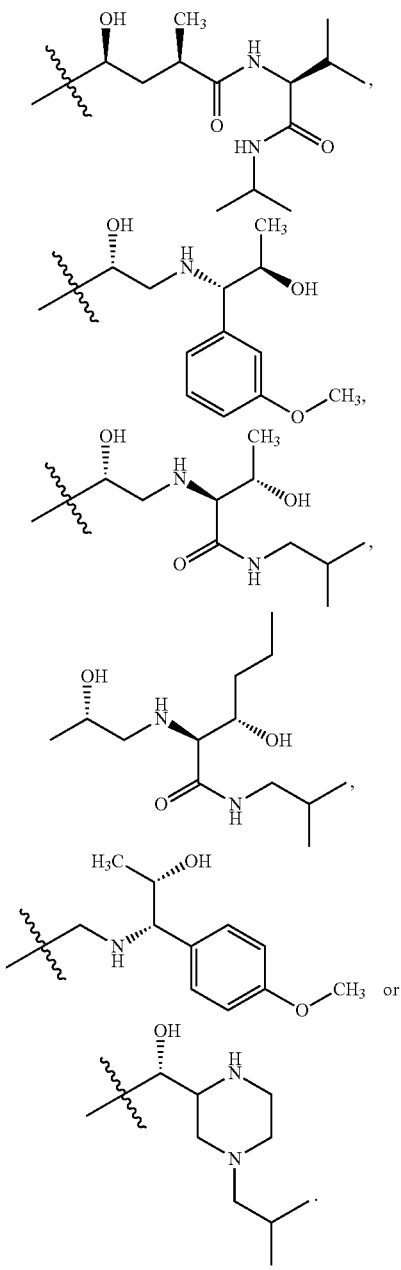

In some embodiments, the compound has formula III, wherein $R_8$ is hydrogen. In other embodiments, the compound has formula III, wherein $R_8$ is alkyl$_{(C\leq 8)}$. In other embodiments, the compound has formula III, wherein $R_8$ is

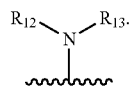

In some embodiments, $R_{12}$ is hydrogen. In other embodiments, $R_{12}$ is alkyl$_{(C\leq 8)}$. In some embodiments, $R_{12}$ is methyl. In other embodiments. $R_{12}$ is alkylsulfonyl$_{(C\leq 8)}$. In some embodiments, $R_{12}$ is methylsulfonyl. In some embodiments, $R_{13}$ is alkyl$_{(C\leq 8)}$. In some embodiments, $R_{13}$ is methyl. In other embodiments, $R_{13}$ is alkylsulfonyl(cs). In some embodiments, $R_{13}$ is methylsulfonyl. In some embodiments, the compound has formula III, wherein $R_9$ is hydrogen. In other embodiments, the compound has formula III, wherein $R_9$ is iodo.

In some embodiments, the compound has formula IV, wherein $R_{11}$ is —SCH$_3$ or —SO$_2$CH$_3$.

In some embodiments, said subject is further treated with at least a second type 2 diabetes therapy. In some embodiments, the second type 2 diabetes therapy is insulin. In other embodiments, the second type 2 diabetes therapy is metformin. In other embodiments, the second type 2 diabetes therapy is selected from a sulfonylurea, a non-sulfonylurea secretagogue, an alpha glucosidase inhibitor, and a thiazolidinedione. In other embodiments, said subject is treated with (a) insulin and (b) metformin, a sulfonylurea, a non-sulfonylurea secretagogue, an alpha glucosidase inhibitor, or a thiazolidinedione.

In some embodiments, the invention is a method of treating comprises one or more of improving insulin production, improving glucose homeostasis; reducing, suppressing, attenuating, or inhibiting hyperglucogonemia or a condition associated with hyperglucogonemia; or reducing HbA1c; in a subject diagnosed with or otherwise having type 2 diabetes. In some embodiments, said compound is administered orally or by injection, including intravenously, intradermally, intraarterially, intraperitoneally, intracranially, intraarticularly, intraprostaticaly, intrapleurally, intramuscularly, or subcutaneously. In some embodiments, said compound is administered 1, 2, 3 or 4 times daily. In some embodiments, the invention is further comprised of measuring blood glucose before and/or after administering said compound to said subject. In some embodiments, said mammalian subject is a human.

In some embodiments, the present invention is a method of increasing pancreatic beta cell mass in a mammalian subject comprising administering to said subject a compound having a formula selected from:

wherein $R_1$ is

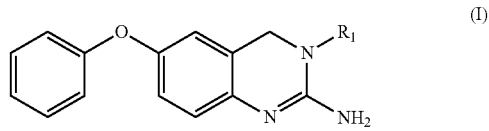

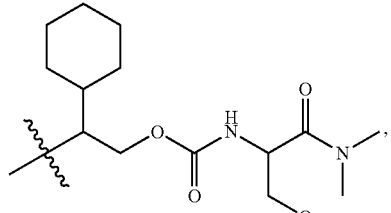

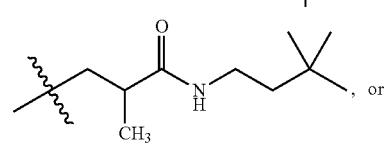

-continued

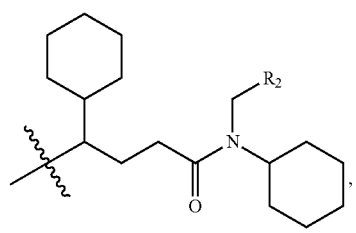

wherein $R_2$ is heteroaryl$_{(C \leq 8)}$, heterocycloalkyl$_{(C \leq 8)}$, a substituted version of either of these groups, or

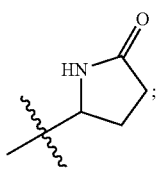

(IIa)

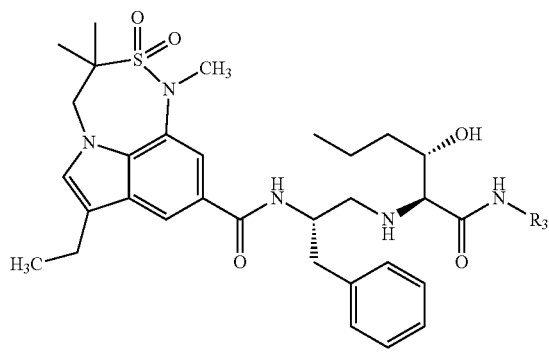

wherein $R_3$ is alkyl$_{(C \leq 8)}$ or a substituted version thereof;

(IIb)

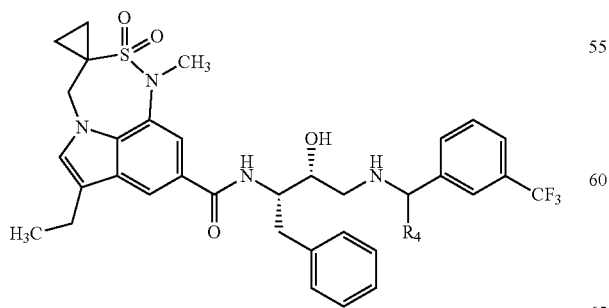

wherein $R_4$ is hydrogen, alkyl$_{(C \leq 8)}$ or substituted alkyl$_{(C \leq 8)}$;

(III)

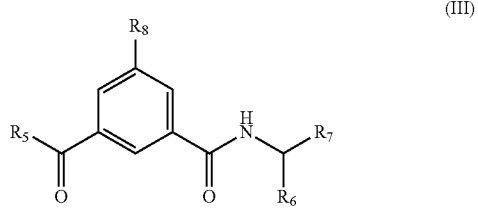

wherein: $R_5$ is

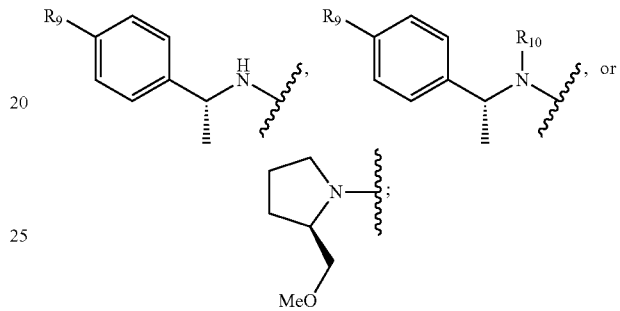

wherein: $R_9$ is hydrogen or halo; $R_{10}$ is alkyl$_{(C \leq 4)}$; $R_6$ is hydrogen, alkyl$_{(C \leq 8)}$, aralkyl$_{(C \leq 8)}$, or a substituted version of either of these groups; or a halogen; and $R_7$ is:

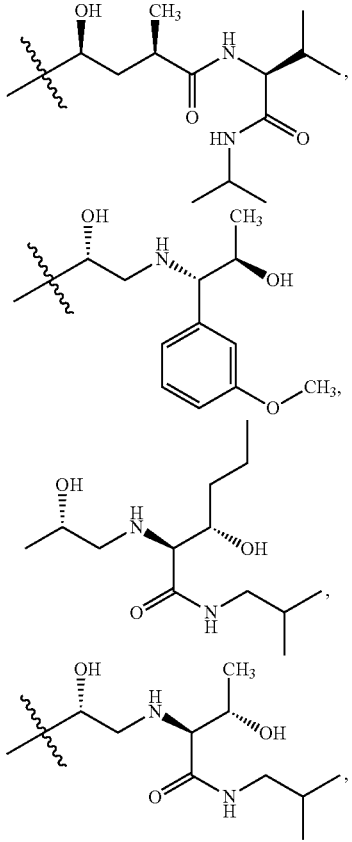

-continued

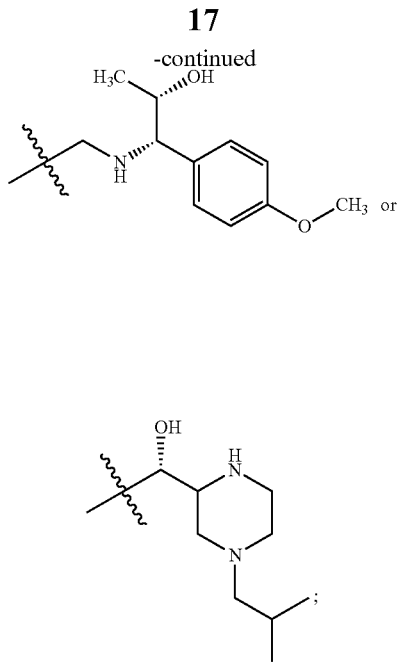

$R_8$ is hydrogen, alkyl$_{(C≤8)}$, or

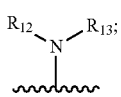

wherein: $R_{12}$ and $R_{13}$ are each independently hydrogen, alkyl$_{(C≤8)}$, or alkylsulfonyl$_{(C≤8)}$; and (IV)

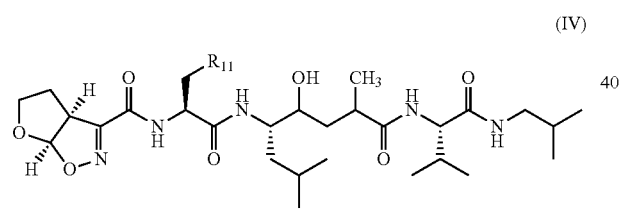

wherein $R_{11}$ is alkylthio$_{(C≤8)}$ or alkylsulfonyl$_{(C≤8)}$, or a pharmaceutically acceptable salt or tautomer of any of the above formulas. In some embodiments, the compound has formula III, wherein the formula is:

(IIIa)

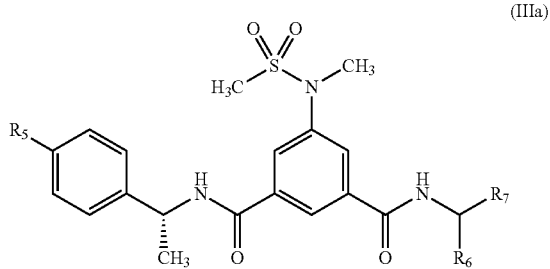

wherein: $R_5$ is hydrogen or halo; $R_6$ is hydrogen, alkyl$_{(C≤8)}$, aralkyl$_{(C≤8)}$, or a substituted version of either of these groups; or a halogen;

and $R_7$ is:

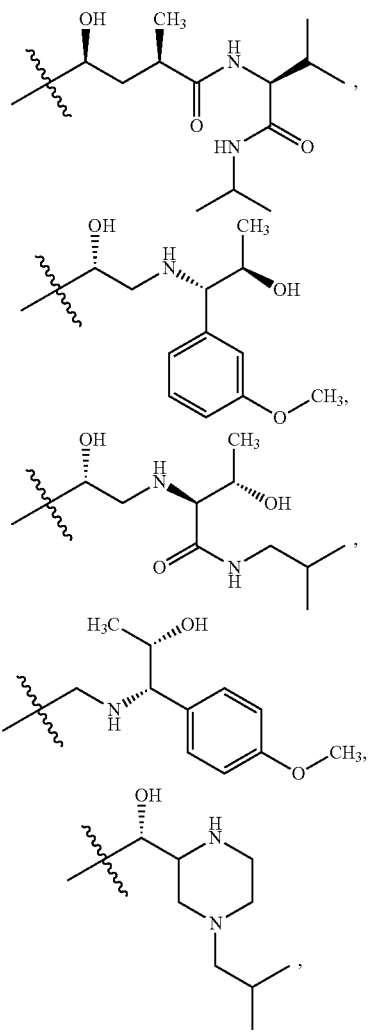

or a pharmaceutically acceptable salt or tautomer.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the inherent variation of error for the device, the method being employed to determine the value, or the variation that exists among the study subjects.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the invention that follows.

DESCRIPTION OF ILLUSTRATIVE EMBODIMENTS

Figure 1:
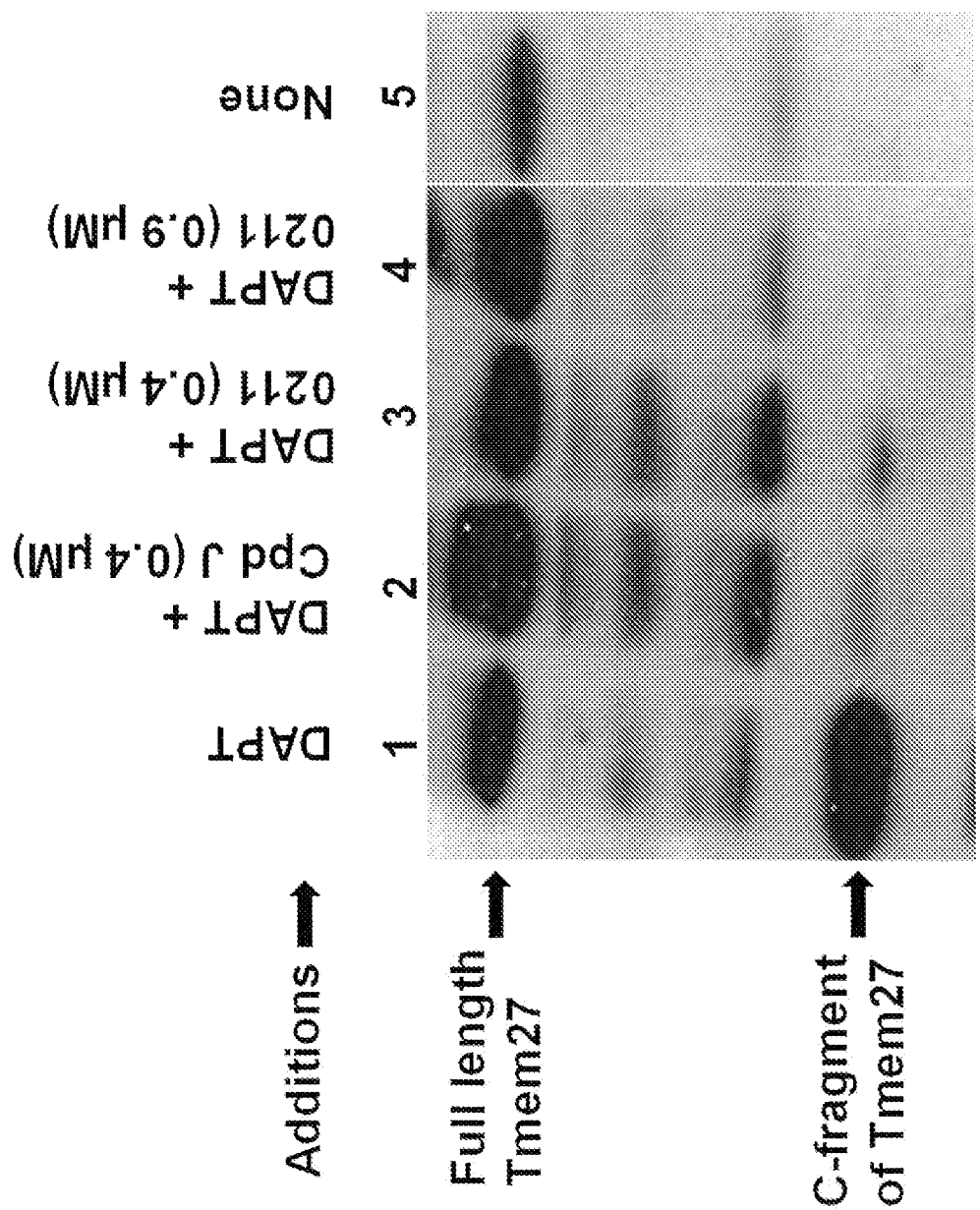
FIG. 1—Inhibition of memapsin 1 processing of Tmem27 by inhibitor 0211 in MIN6 cells. The image in this figure is a Western blot of MIN6 cell lysate. The C-terminal fragment band, which was revealed in the presence of gamma-secretase inhibitor DAPT, was completely abolished by 0.9 µM of inhibitor 0211. Compound J (Cpd J) a memapsin 1 inhibitor reported by Esterhazy et al. (2011) which is incorporated by reference herein was used as a positive control.

Aspartic proteases are a family of protease enzymes that use two aspartate residues for catalysis of the hydrolysis of their peptide substrates. In general, they have two highly-conserved aspartates in the active site and, usually but not always, their optimally active at an acidic pH. Aspartic proteases are involved in disease such as hypertension, HIV, tumorigenesis, peptic ulcer disease, amyloid disease, malaria and common fungal infections such as candidiasis.

Eukaryotic aspartic proteases include pepsins, cathepsins, and renins. They have a two-domain structure, arising from ancestral gene duplication and fusion. Each domain contributes a catalytic Asp residue, with an extended active site cleft localized between the two lobes of the molecule. One lobe has probably evolved from the other through a gene duplication event in the distant past. In modern-day enzymes, although the three-dimensional structures are very similar, the amino acid sequences are more divergent, except for the catalytic site motif, which is highly conserved. The presence and position of disulfide bridges are other somewhat conserved features of aspartic peptidases.

As discussed above, the protease that cleaves off the ectodomain of Tmem27, memapsin 1/BACE2, has recently been identified (Esterhazy et al., 2011). In that study, a memapsin 1 siRNA caused increased beta cell mass and improved control of glucose homeostasis due to increased insulin levels in a mouse diabetes model. These results implicate memapsin 1 in the control of beta cell maintenance and further suggest a strategy to inhibit memapsin 1 for the expansion of functional pancreatic beta cell mass in the clinical treatment of type 2 diabetes. Also, International Patent Application WO2011029803 describes 2-aminodihydro[1,3]thiazines as BACE2 inhibitors for the treatment of diabetes.

Here, the inventors have taken a different approach, focusing on compounds previously identified as memapsin 2 (BACE1) inhibitors. Given the similarity between substrate specificity of memapsin 1 and memapsin 2, the inventors demonstrated that compounds created for inhibiting memapsin 2 had some degree of activity against memapsin 1 (Ghosh et al., 2001; 2005; 2007; 2008). The inventors then determined memapsin 1 inhibitory activity for compounds created for memapsin 2 inhibition. In addition, they also created new memapsin 1 inhibitors. The identity of these compounds, and their use in treating diabetes, are discussed in detail below.

I. DIABETES

Type I diabetes is a form of diabetes mellitus. Type I diabetes is an autoimmune disease that results in the permanent destruction of insulin-producing β cells of the pancreas. Type I is lethal unless treatment with exogenous insulin via injections replaces the missing hormone, or a functional replacement for the destroyed pancreatic beta cells is provided (such as via a pancreas transplant).

In contrast, diabetes mellitus type 2 (formerly non-insulin-dependent diabetes mellitus or adult-onset diabetes) is a metabolic disorder that is characterized by high blood glucose in the context of insulin resistance and relative insulin deficiency. The classic symptoms are excess thirst, frequent urination, and constant hunger. Type 2 diabetes makes up about 90% of cases of diabetes with the other 10% due primarily to diabetes mellitus type 1 and gestational diabetes. Obesity is thought to be the primary cause of type 2 diabetes in people who are genetically predisposed to the disease.

Type 2 diabetes is initially managed by increasing exercise and dietary modification. However, there are several classes of anti-diabetic medications available when exercise and diet alone fail. Metformin is generally recommended as a first line treatment as there is good evidence that it decreases mortality. Injections of insulin may either be added to oral medication or used alone. Other classes of medications used to treat type 2 diabetes are sulfonylureas, nonsulfonylurea secretagogues, alpha glucosidase inhibitors, and thiazolidinediones. Metformin however should not be used in those with severe kidney or liver problems.

When insulin is used, a long-acting formulation is typically added initially at night, while oral medications are continued. Doses are then increased to effect. When nightly insulin is insufficient twice daily insulin may achieve better control. The long acting insulins, glargine and detemir, do not appear much better than NPH but have a significantly greater cost making them as of 2010 not cost effective. In those who are pregnant insulin is generally the treatment of choice.

Rates of diabetes have increased markedly over the last 50 years in parallel with obesity. As of 2010 there are approximately 285 million people with the disease compared to around 30 million in 1985. Long-term complications from high blood sugar can include heart attacks, strokes, diabetic retinopathy where eyesight is affected, kidney failure which may require dialysis, and poor circulation of limbs leading to amputations. The acute complication ketoacidosis is uncommon unlike in type 1 diabetes, nonketonic hyperglycemia however may occur. The classic symptoms of diabetes are polyuria (frequent urination), polydipsia (increased thirst), polyphagia (increased hunger), and weight loss.

Type 2 diabetes is typically a chronic disease, associated with a ten year shorter life expectancy. This is partly due to a number of complications with which it is associated including: two to four times the risk of cardiovascular disease and stroke, a 20-fold increase in lower limb amputations, and increased rates of hospitalizations. In the developed world, and increasingly elsewhere, type 2 diabetes is the largest cause of non-traumatic blindness and kidney failure, as compared to non-diabetics. It has also been associated with an increased risk of cognitive dysfunction and dementia through disease processes such as Alzheimer's disease and vascular dementia. Other complications include: acanthosis nigricans, sexual dysfunction, and frequent infections.

The development of type 2 diabetes is caused by a combination of lifestyle and genetic factors. While some are under personal control, such as diet and obesity, others such as age, gender, and genetics are not. A lack of sleep has been linked to type 2 diabetes as has nutritional status during fetal development.

The most useful laboratory test to distinguish type I from type II diabetes is the C-peptide assay, which is a measure of endogenous insulin production since external insulin (to date) has included no C-peptide. However, C-peptide is not absent in type I diabetes until insulin production has fully ceased, which may take months. The presence of anti-islet antibodies (to Glutamic Acid Decarboxylase, Insulinoma Associated Peptide-2 or insulin), or lack of insulin resistance, determined by a glucose tolerance test, would also be suggestive of type 1. As opposed to that, many type 2 diabetics still produce insulin internally, and all have some degree of insulin resistance. Testing for GAD 65 antibodies has been proposed as an improved test for differentiating between type 1 and type 2 diabetes.

II. MEMAPSIN 1

Memapsin 1 is a type 1 transmembrane protease consisted of an N-terminal ectodomain, a transmembrane domain and a C-terminal cytosolic domain. Memapsin 1 and its closest homologue memapsin 2 (BACE1) were first reported by Lin et al. (2000) and independently from other groups (Vassar et al., 1999; Yan et al., 1999; Hussain et al., 1999). The ectodomain of memapsin 1 is a pepsin-like aspartic protease. Memapsin 1 has a somewhat broad subsite specificity (Turner et al., 2002) which is very similar to those for memapsin 2 (Turner et al., 2001). The low resolution crystal structure of memapsin 1 has been determined (Ostermann et al., 2006).

Cerebral deposition of amyloid beta peptide is an early and critical feature of Alzheimer's disease and a frequent complication of Down syndrome. Amyloid beta peptide is generated by proteolytic cleavage of amyloid precursor protein by 2 proteases, one of which is the protein encoded by this gene. This gene localizes to the "Down critical region" of chromosome 21. The encoded protein, a member of the peptidase A1 protein family, is a type I integral membrane glycoprotein and aspartic protease. Three transcript variants encoding different isoforms have been described for this gene. BACE2 has been shown to interact with GGA1 and GGA2.

III. INHIBITORS OF MEMAPSIN 1

A. Definitions

When used in the context of a chemical group, "hydrogen" means —H; "hydroxy" means —OH; "oxo" means =O "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double-bond, and "≡" means triple bond. The symbol "----" represents an optional bond, which if present is either single or double. The symbol "⩬" represents a single bond or a double-bond. Thus, for example, the structure

includes the structure

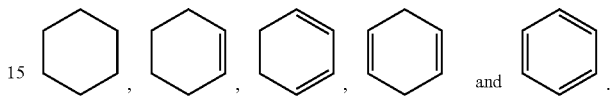

As will be understood by a person of skill in the art, no one such ring atom forms part of more than one double-bond. The symbol "⌇", when drawn perpendicularly across a bond indicates a point of ⌇ attachment of the group. It is noted that the point of attachment is typically only identified in this manner for larger groups in order to assist the reader in rapidly and unambiguously identifying a point of attachment. The symbol "◢" means a single bond where the group attached to the thick end of the wedge is "out of the page." The symbol "▨" means a single bond where the group attached to the thick end of the wedge is "into the page". The symbol "⌇" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

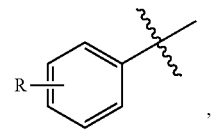

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

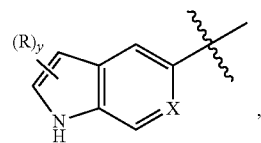

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example, a carbon oxygen double-bond or a carbon nitrogen double-bond. Moreover, it does not preclude a carbon-carbon double-bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double-bonds (alkenes/alkenyl) or with one or more triple bonds (alkynes/alkynyl). When the term "aliphatic" is used without the "substituted" modifier, only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —Cl$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one non-aromatic carbon-carbon double-bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double-bond, no carbon-carbon triple bonds, and no atoms other than carbon and hydrogen. The groups, —CH=CH—, —CH=C(CH$_3$)CH$_2$—, —CH=CHCH$_2$—, and

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH₃, —OCH₂CH₃, —C(O)CH₃, —N(CH₃)₂, —C(O)NH₂, —OC(O)CH₃, or —S(O)₂NH₂. The groups, —CH═CHF, —CH═CHCl and —CH═CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double-bonds. The groups, —C≡CH, —C≡CCH₃, and —CH₂C≡CCH₃, are non-limiting examples of alkynyl groups. When alkynyl is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. An "alkyne" refers to the compound H—R, wherein R is alkynyl.

The term "aryl" when used without the "substituted" modifier refers to a monovalent unsaturated aromatic group with an aromatic carbon atom as the point of attachment, the carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl) phenyl, —C₆H₄CH₂CH₃ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

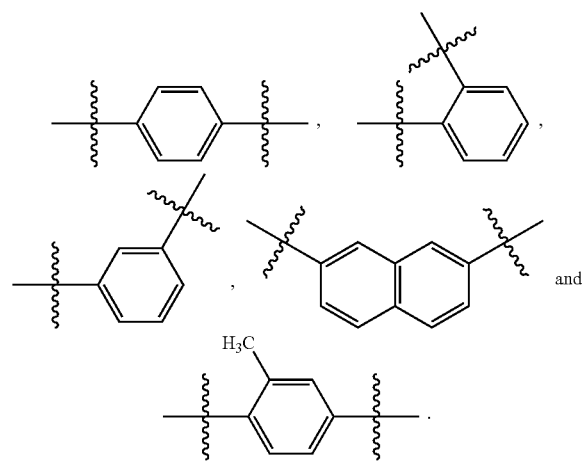

When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

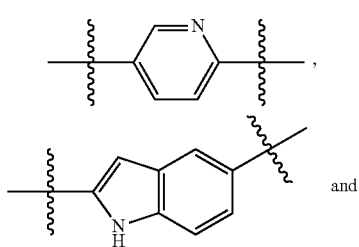

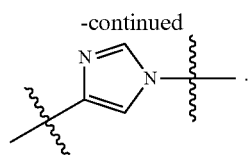

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. If more than one ring is present, the rings may be fused or unfused. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, and pyranyl. When the term "heterocycloalkyl" used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including the hydrogen atom directly attached the carbonyl or thiocarbonyl group) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", and "heteroarylsulfonyl", are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

As used herein, a "chiral auxiliary" refers to a removable chiral group that is capable of influencing the stereoselectivity of a reaction. Persons of skill in the art are familiar with such compounds, and many are commercially available.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts Properties, and Use* (P. H. Stahl & C. G. Wermuth eds., Verlag Helvetica Chimica Acta, 2002).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylenebis-β-hydroxynaphthoate, gentisates, isethionates, di-p-toluoyltartrates, methane-sulfonates, ethanesulfonates, benzenesulfonates, p-toluenesulfonates, cyclohexyl-sulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diasteromers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Substituent convertible to hydrogen in vivo" means any group that is convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydropyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl (—C(O)OC(CH$_3$)$_3$), benzyloxycarbonyl, p-methoxybenzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine). Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Suitable peptide residues include peptide residues comprising two to five amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and haloethoxycarbonyl groups (such as β,β,β-trichloroethoxycarbonyl and β-iodoethoxycarbonyl).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

B. Compounds of the Present Invention

The structural formulas of the compounds are as follows:

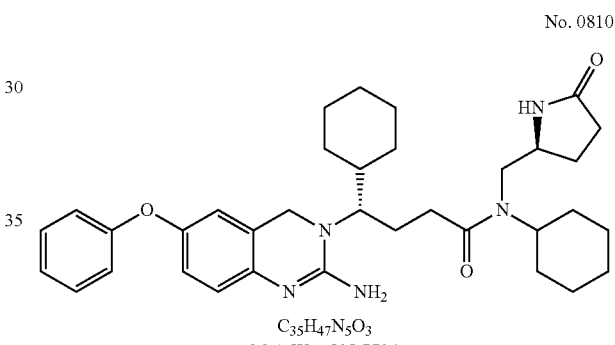

No. 0810

C$_{35}$H$_{47}$N$_5$O$_3$
Mol. Wt.: 585.7794

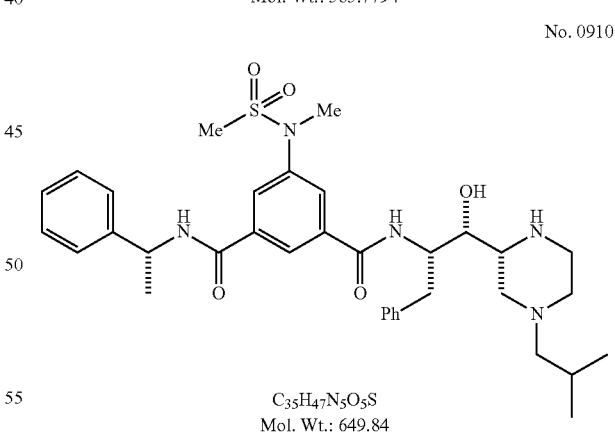

No. 0910

C$_{35}$H$_{47}$N$_5$O$_5$S
Mol. Wt.: 649.84

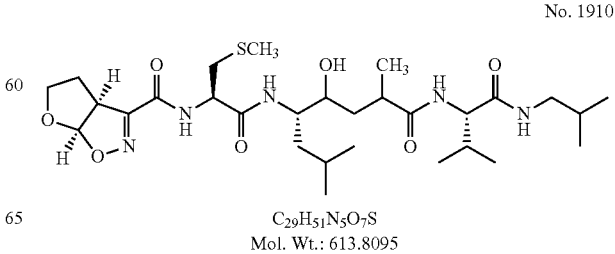

No. 1910

C$_{29}$H$_{51}$N$_5$O$_7$S
Mol. Wt.: 613.8095

No. 1110

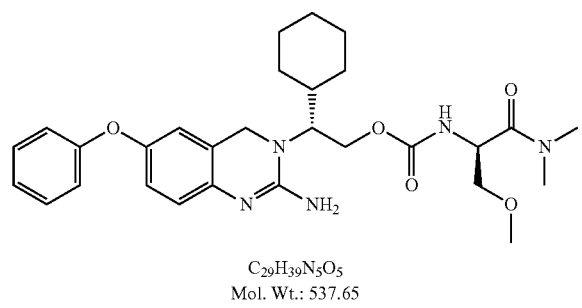

C₂₉H₃₉N₅O₅
Mol. Wt.: 537.65

No. 2710

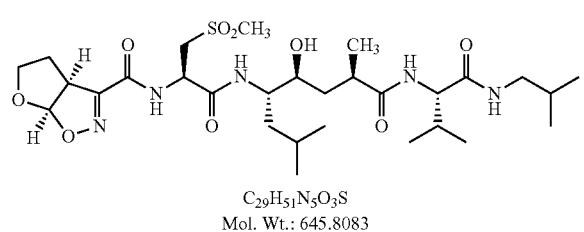

C₂₉H₅₁N₅O₃S
Mol. Wt.: 645.8083

No. 1549

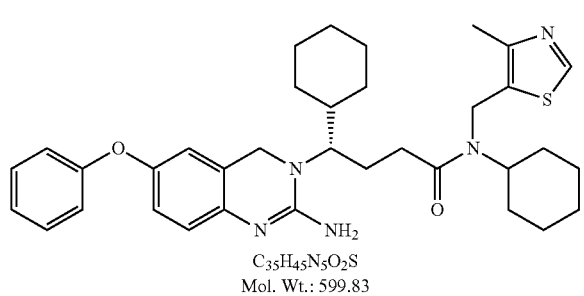

C₃₅H₄₅N₅O₂S
Mol. Wt.: 599.83

No. 1589

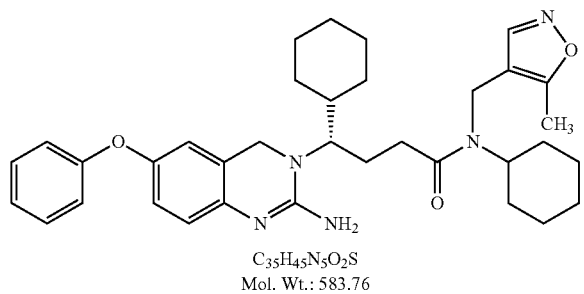

C₃₅H₄₅N₅O₂S
Mol. Wt.: 583.76

No. 0111

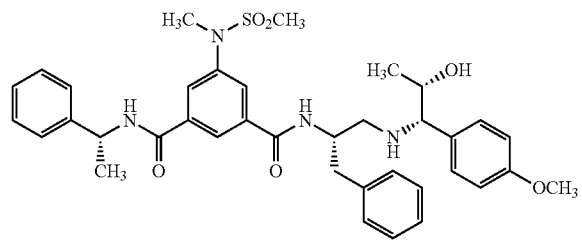

Chemical Formula: C₃₇H₄₄N₄O₆S
Molecular Weight: 672.83

No. 0113

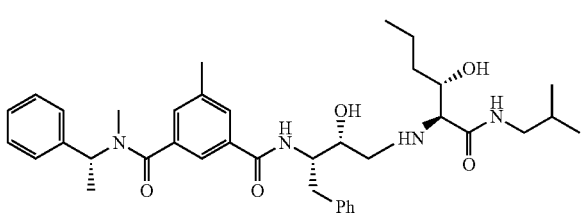

Chemical Formula: C₃₆H₅₂N₄O₅
Molecular Weight: 644.84

No. 0211

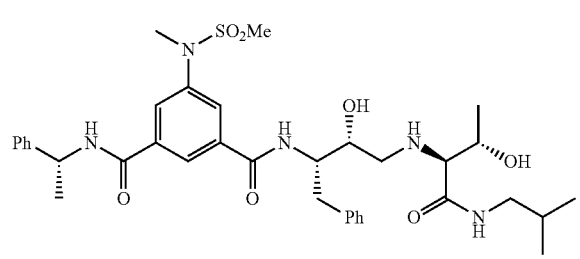

Chemical Formula: C₃₆H₄₉N₅O₇S
Molecular Weight: 695.87

No. 0213

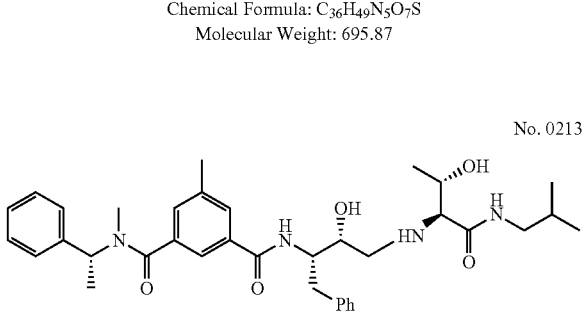

Chemical Formula: C₃₆H₄₈N₄O₅
Molecular Weight: 616.79

No. 0711

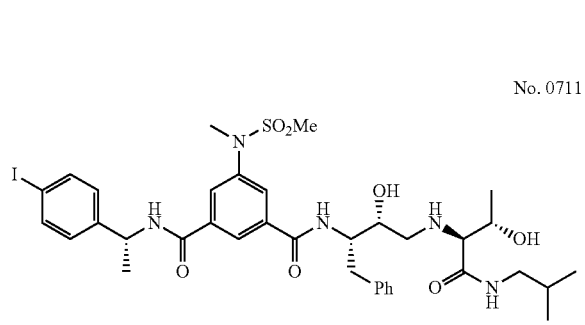

Chemical Formula: C₃₆H₄₈IN₅O₇S
Molecular Weight: 821.77

No. 2211

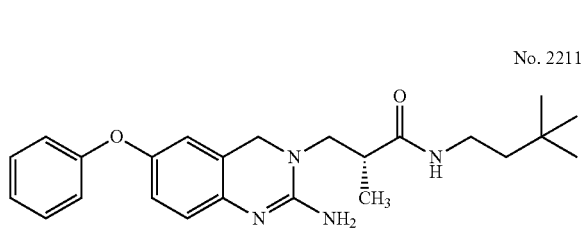

Chemical Formula: C₂₄H₃₂N₄O₂
Molecular Weight: 408.54

No. 2611

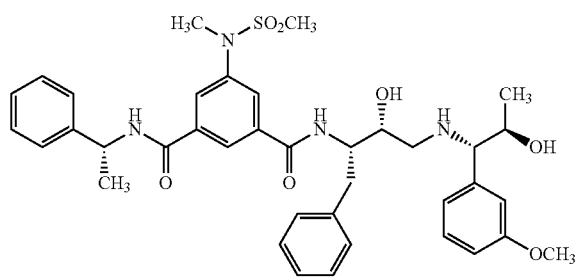

Chemical Formula: C₃₈H₄₆N₄O₇S
Molecular Weight: 702.86

No. 3511

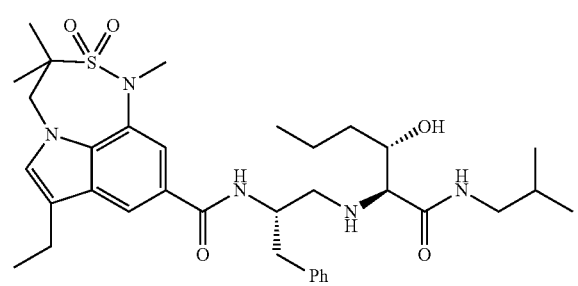

Chemical Formula: C₃₅H₅₁N₅O₅S
Molecular Weight: 653.87

No. 4311

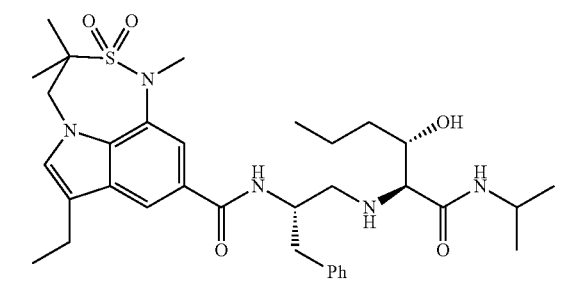

Chemical Formula: C₃₄H₄₉N₅O₅S
Molecular Weight: 639.85

No. 5211

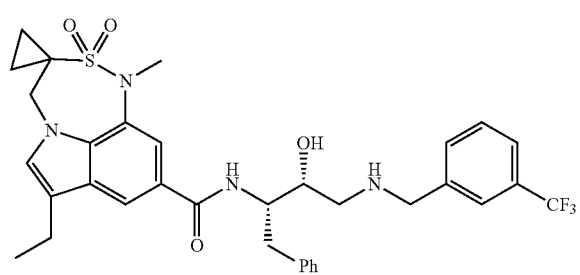

Chemical Formula: C₃₄H₃₇F₃N₄O₄S
Molecular Weight: 654.74

No. 5511

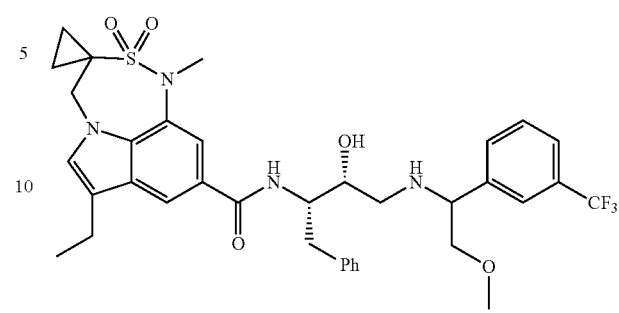

Chemical Formula: C₃₆H₄₁F₃N₄O₅S
Molecular Weight: 698.79

No. 6212

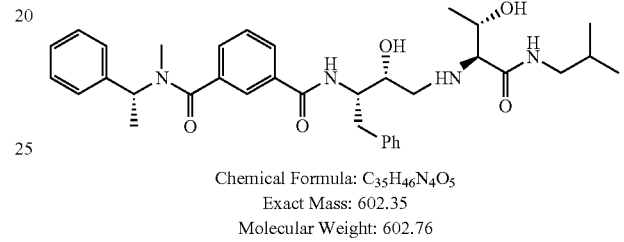

Chemical Formula: C₃₅H₄₆N₄O₅
Exact Mass: 602.35
Molecular Weight: 602.76

No. 6412

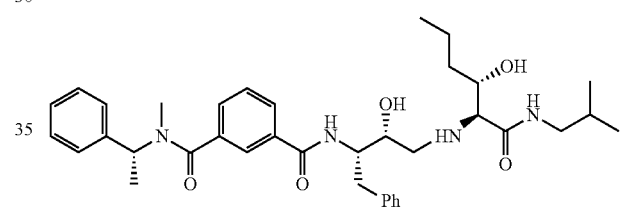

Chemical Formula: C₃₇H₅₀N₄O₅
Molecular Weight: 630.82

No. 6512

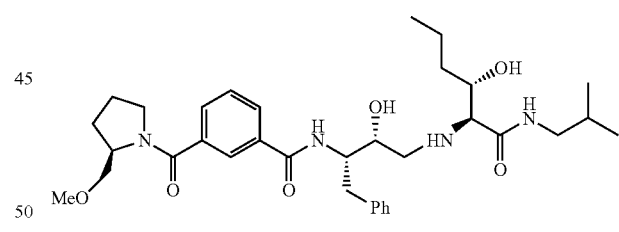

Chemical Formula: C₃₄H₅₀N₄O₈
Molecular Weight: 610.78

No. 6612

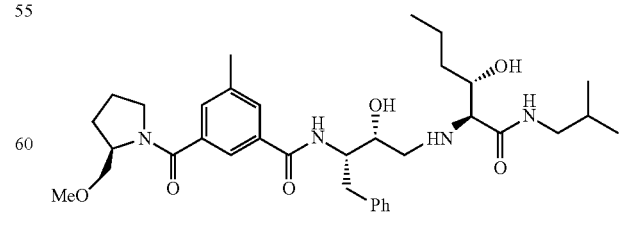

Chemical Formula: C₃₅H₅₂N₄O₆
Molecular Weight: 624.81

-continued

No. 8234

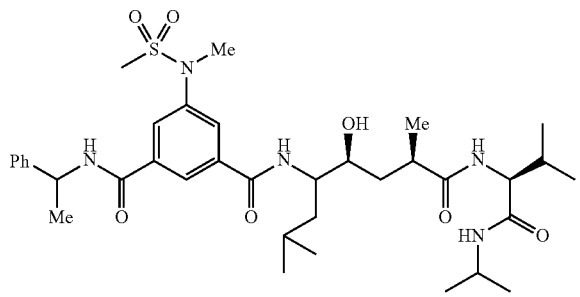

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

The synthesis of inhibitor No. 5211 is shown in Scheme 1 and 2.

Scheme 1

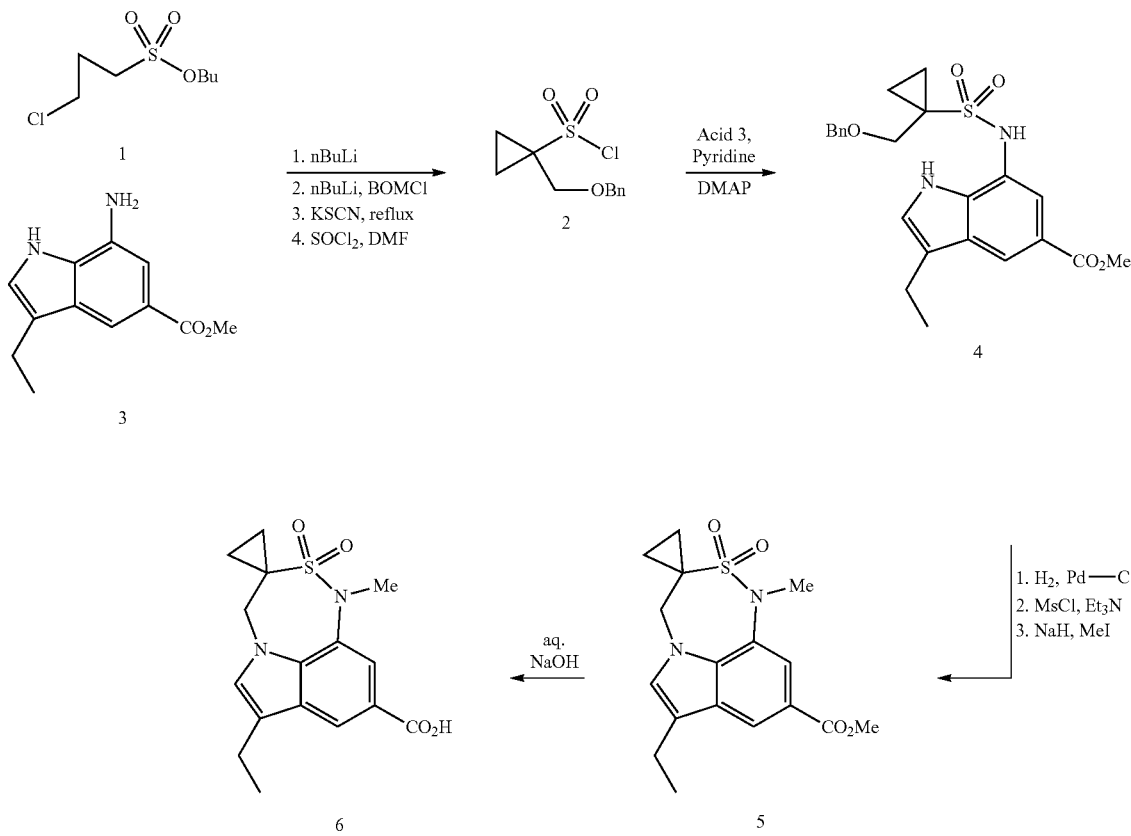

Synthesis of butyl 1-(benzyloxymethyl)cyclopropanesulfonate 2

Solutions of BuLi (17.2 mmol, 6.9 mL (2.5 M in hexanes) in 15 mL THF) and butyl 3-chloro-1-propanesulfonate 1 (16.3 mmol, 3.5 g in 15 mL THF) were added at the same time via cannula to an oven dried flask containing THF (100 mL) at −78° C. and the resulting mixture was stirred for 5-10 min at −78° C. and 30 min at 0° C. Reaction mixture was cooled back to −78° C. and a solution of BuLi (19.6 mmol, 7.8 mL (2.5 M in hexanes)) was added to this mixture. After stirring for 15 min at −78° C., BOMCl (19.6 mmol, 2.7 mL) was added to the reaction flask and stirring was continued for further 2 h at −78° C. and 3 h at 23° C. Reaction mixture was quenched with $H_2O$ and THF was removed under reduced pressure. The resulting mixture was diluted with $CHCl_2$ and $H_2O$. Organic layer was separated and the aqueous layer was extracted with $CH_2Cl_2$. The combined extracts were dried over anhydrous $Na_2SO_4$, filtered and concentrated under reduced pressure.

The residue was purified by silica gel column chromatography (8-12% ethyl acetate/hexanes) to furnish butyl 1-(benzyloxymethyl)cyclopropanesulfonate in 80% yields (3.9 g).

$^1$H NMR (300 MHz, $CDCl_3$) δ 7.40-7.25 (m, 5H), 4.55 (s, 2H), 4.23 (t, J=6.6 Hz, 2H), 3.79 (s, 2H), 1.73-1.58 (m, 2H), 1.48 (ABq, J=6.9, 5.0 Hz, 2H), 1.44-1.30 (m, 2H), 1.11 (ABq, J=7.0, 5.1 Hz, 2H), 0.90 (t, J=7.4 Hz, 3H). $^{13}$C NMR (75 MHz, $CDCl_3$) δ 137.41, 128.33, 127.78, 127.61, 73.09, 70.66, 69.84, 37.81, 31.04, 18.55, 13.41, 10.72.

To a mixture of 1-(benzyloxymethyl)cyclopropanesulfonate (13 mmol, 3.88 g) in DME (40 mL) and $H_2O$ (40 mL), KSCN (13.65 mmol, 1.33 g) was added at 23° C. and the resulting reaction mixture was refluxed for 15 h. Reaction mixture was cooled to 23° C. and diluted with $H_2O$ and ethyl acetate. Organic layer was separated and the aqueous layer was concentrated under reduced pressure to provide the crude potassium 1-(benzyloxymethyl)cyclopropanesulfonate which was used directly in the next step without additional purification.

A mixture of potassium 1-(benzyloxymethyl)cyclopropanesulfonate in $SOCl_2$ (35 mL) and DMF (3.5 mL) was refluxed for 1.5 h and excess $SOCl_2$ was removed under reduced pressure. Water was added carefully to the resulting mixture and extracted with ethyl acetate. The combined extracts were dried over anhydrous $Na_2SO_4$, filtered and concentrated under reduced pressure. The residue was purified by silica gel column chromatography (5-10% ethyl acetate/hexanes) to obtain 1-(benzyloxymethyl)cyclopropanesulfonyl chloride 2 in 97% yields (3.3 g).

$^1$H NMR (300 MHz, $CDCl_3$) δ 7.46-7.28 (m, 5H), 4.63 (s, 2H), 4.01 (s, 2H), 1.85-1.77 (m, 2H), 1.46-1.37 (m, 2H). $^{13}$C NMR (75 MHz, $CDCl_3$) δ 136.99, 128.41, 127.89, 127.61, 73.29, 68.38, 52.39, 14.03.

Synthesis of Sulfonamide 4

To a mixture of amine 3 (3.66 mmol, 0.8 g), pyridine (11 mmol, 0.89 mL) and DMAP (0.73 mmol, 89.2 mg) in $CH_2Cl_2$ at 0° C. was added a solution of 1-(benzyloxymethyl)-cyclopropanesulfonyl chloride (2) (3.84 mmol, 1 g in 5 mL $CH_2Cl_2$) and the resulting mixture was stirred for 44 h at 23° C. Reaction mixture was diluted with $CH_2Cl_2$, washed with aqueous 1N HCl, brine and dried over anhydrous $Na_2SO_4$. Dichloromethane solution was filtered and concentrated under reduced pressure. The residue was purified by silica gel column chromatography (20-30% ethyl acetate/hexanes) to afford the corresponding sulfonamide 4 in 74% yields (1.2 g).

$^1$H NMR (400 MHz, $CDCl_3$) δ 9.38 (s, 1H), 8.25 (s, 1H), 7.87 (s, 1H), 7.49 (d, J=7.1 Hz, 2H), 7.42 (t, J=7.4 Hz, 2H), 7.39-7.33 (m, 1H), 6.79 (s, 1H), 6.69 (s, 1H), 4.73 (s, 2H), 3.91 (s, 3H), 3.90 (s, 2H), 2.75 (q, J=7.5 Hz, 2H), 1.30 (t, J=7.5 Hz, 3H), 1.11-0.99 (m, 2H), 0.77-0.65 (m, 2H). $^{13}$C NMR (100 MHz, $CDCl_3$) δ 167.62, 136.35, 135.01, 128.91, 128.63, 128.44, 122.14, 121.20, 120.85, 120.76, 120.61, 120.36, 74.15, 73.10, 51.84, 38.91, 18.09, 14.25, 10.25.

Synthesis of 7,6,5-tricyclic Indole Carboxylic Acid 6

To a solution of sulfonamide 4 (2.7 mmol, 1.19 g) in MeOH (75 mL) and AcOH (25 mL), 10% Pd/C (0.2 g) was added under argon. Argon ballon was now replaced with H2 ballon and the resulting mixture was stirred for 16 h at 23° C. Reaction mixture was filtered through celite and washed with MeOH. Solvent was removed under reduced pressure and the resulting residue was diluted with toluene and concentrated under reduced pressure to furnish the corresponding alcohol in 95% yield.

To a mixture of the above alcohol (0.6 mmol, 0.21 g) and $Et_3N$ (0.9 mmol, 0.12 mL) in $CH_2Cl_2$ (25 mL) at 0° C., was added methanesulfonyl chloride (0.63 mmol, 0.049 mL) and the resulting mixture was stirred for 2 h at 23° C. Reaction mixture was diluted with $CH_2Cl_2$, washed with aqueous 1N HCl, brine and dried over anhydrous $Na_2SO_4$. Dichloromethane solution was filtered and concentrated under reduced pressure. The residue was purified by silica gel column chromatography (5-15% diethyl ether/$CH_2Cl_2$) to afford the corresponding mesylate in 46% (70% BRSM) yields (0.12 g, 69 mg of alcohol was recovered).

$^1$H NMR (400 MHz, $CDCl_3$) δ 9.24 (s, 1H), 8.26 (s, 1H), 7.87 (d, J=1.0 Hz, 1H), 7.41 (s, 1H), 7.07 (s, 1H), 4.58 (s, 2H), 3.93 (s, 3H), 3.16 (s, 3H), 2.79 (q, J=7.5 Hz, 2H), 1.38-1.28 (m, 5H), 1.06-0.97 (m, 2H).

To a solution of the above mesylate (0.69 mmol, 0.297 g) in DMF (30 mL), was added NaH (2.76 mmol, 0.11 g, 60% dispersion in mineral oil) at 23° C. After stirring the mixture for 3 h at 23° C., iodo methane (3.5 mmol, 0.22 mL) was added to the flask and stirring was continued for further 1 h at 23° C. Reaction mixture was carefully quenched with MeOH, diluted with ethyl acetate and washed with aqueous 1N HCl. Ethyl acetate solution was filtered and concentrated under reduced pressure. The resulting residue was purified by silica gel column chromatography (35-40% ethyl acetate/hexanes) to afford the corresponding 7,6,5-tricyclic indole derivative 5 in 87% yields (0.21 g).

$^1$H NMR (400 MHz, $CDCl_3$) δ 8.26 (d, J=1.1 Hz, 1H), 7.83 (d, J=1.0 Hz, 1H), 6.78 (s, 1H), 4.32 (s, 2H), 3.93 (s, 3H), 3.48 (s, 3H), 2.77 (q, J=7.5 Hz, 2H), 1.53 (t, J=6.6 Hz, 2H), 1.31 (t, J=7.5 Hz, 3H), 1.03-0.95 (m, 2H).

A mixture of the above 7,6,5-tricyclic indole derivative 5 (0.2 mmol, 69.7 mg) and NaOH (20 mmol, 0.8 g in 10 mL $H_2O$) in EtOH (5 mL) and THF (10 mL) was stirred for 4 days at 23° C. Solvent was removed under reduced pressure and the resulting mixture was diluted with $H_2O$ and diethyl ether. Organic layer was separated, aqueous layer was acidified with aqueous 1N HCl and extracted with ethyl acetate. The combined extracts were dried over anhydrous $Na_2SO_4$, filtered and concentrated under reduced pressure to furnish the corresponding crude acid 6 in 75% yields (50 mg) which was used directly in the coupling reaction without any further purification.

Synthesis of Inhibitor 9

No. 5211

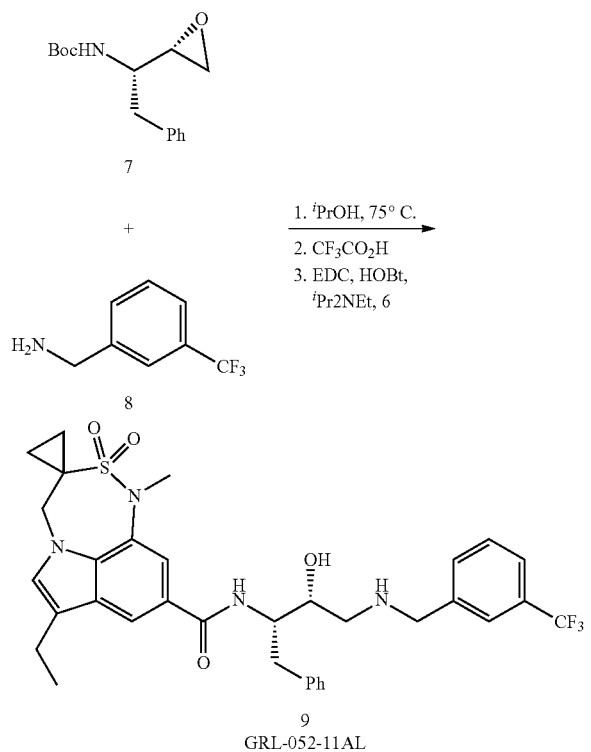

Scheme 2

To a solution of tert-butyl {(S)-1-[(S)-oxiran-2-yl]-2-phenylethyl}carbamate (7) (0.13 mmol, 34.2 mg) in iPrOH (2 mL), 3-(trifluoromethyl)benzylamine (8) (0.36 mmol, 0.05 ml) was added at 23° C. The resulting mixture was heated at 75° C. for 9 h.

Isopropanol was removed under reduced pressure and the residue was purified by silica gel column chromatography (1-3% MeOH/$CH_2Cl_2$) to furnish tert-butyl {(2S,3R)-3-hydroxy-1-phenyl-4-[(3-(trifluoromethyl)-benzylamino]butan-2-yl}carbamate in 70% yields (39.9 mg).

To a solution of the above carbamate (0.091 mmol, 39.9 mg) in $CH_2Cl_2$ (3 mL), trifluoroacetic acid (1 mL) was added at 0° C. and the resulting reaction mixture was stirred for 1.5 h at 23° C. Trifluoroacetic acid and $CH_2Cl_2$ were removed under reduced pressure and the residue was purified by silica gel column chromatography [2-6% (5% $NH_3$/MeOH)/$CH_2Cl_2$] to obtain (2R,3S)-3-amino-4-phenyl-1-[3-(trifluoromethyl)benzylamino]butan-2-ol.

$^1$H NMR (400 MHz, $CDCl_3$) δ 7.60 (s, 1H), 7.53 (d, J=7.7 Hz, 2H), 7.45 (t, J=7.6 Hz, 1H), 7.31 (t, J=7.3 Hz, 2H), 7.25-7.15 (m, 3H), 3.88 (ABq, J=13.6, 20.3 Hz, 2H), 3.65-3.58 (m, 1H), 3.19-3.11 (m, 1H), 2.94-2.84 (m, 2H), 2.77 (dd, J=11.9, 8.4 Hz, 1H), 2.48 (dd, J=13.5, 9.9 Hz, 1H). $^{19}$F NMR (376 MHz, $CDCl_3$) δ −64.07.

To a solution of the above (2R,3S)-3-amino-4-phenyl-1-[3-(trifluoromethyl)benzylamino]butan-2-ol (0.024 mmol, 8.12 mg) in $CH_2Cl_2$ (4 mL), iPr$_2$NEt (0.010 mL), HOBt.$H_2O$ (0.06 mmol, 8.1 mg), 7,6,5-tricyclic indole derivative 6 (0.03 mmol, 10 mg) and EDC.HCl (0.06 mmol, 11.5 mg) were added simultaneously at 23° C. and the resulting mixture was stirred for 13 h at 23° C. Reaction mixture was quenched with saturated aqueous $NaHCO_3$ solution and extracted with $CH_2Cl_2$. The combined extracts were dried over anhydrous $Na_2SO_4$, filtered and concentrated under reduced pressure. The resulting residue was purified by silica gel column chromatography (1-3% MeOH/$CH_2Cl_2$) to furnish the desired inhibitor 9 (No. 5211) in 44% yields (6.94 mg).

$^1$H NMR (400 MHz, $CDCl_3$) δ 7.72 (d, J=1.5 Hz, 1H), 7.61 (s, 1H), 7.56 (d, J=7.5 Hz, 1H), 7.51 (d, J=7.7 Hz, 1H), 7.44 (t, J=7.6 Hz, 1H), 7.36-7.27 (m, 5H), 7.26-7.20 (m, 1H), 6.77 (s, 1H), 6.36 (d, J=8.3 Hz, 1H), 4.44-4.35 (m, 1H), 4.28 (s, 1H), 4.28 (s, 1H), 3.90 (d, J=3.7 Hz, 2H), 3.73-3.67 (m, 1H), 3.42 (s, 3H), 3.14-3.03 (m, 2H), 2.83 (dd, J=12.3, 5.5 Hz, 1H), 2.78 (dd, J=12.3, 4.0 Hz, 1H), 2.71 (q, J=7.5 Hz, 2H), 1.53 (ABq, J=7.0, 5.96 Hz, 2H), 1.29 (t, J=7.5 Hz, 3H), 0.98 (t, J=6.6 Hz, 2H). $^{19}$F NMR (376 MHz, $CDCl_3$) δ −64.07.

IV. TREATMENT OF DIABETES

A. Formulations and Routes of Administration

In accordance with the present invention, patients with type 2 diabetes are treated with the compounds described herein. It will be necessary to prepare pharmaceutical compositions in a form appropriate for administration to a subject. The compositions will generally be prepared essentially free of pyrogens, as well as other impurities that could be harmful to humans or animals. One will generally desire to employ appropriate salts and buffers to render stable cells suitable for introduction into a patient. Aqueous compositions of the present invention comprise an effective amount of stable cells dispersed in a pharmaceutically acceptable carrier or aqueous medium, and preferably encapsulated.

The phrase "pharmaceutically or pharmacologically acceptable" refer to compositions that do not produce adverse, allergic, or other untoward reactions when administered to an animal or a human. As used herein, "pharmaceutically acceptable carrier" includes any and all solvents, dispersion media, antibacterial and antifungal agents, isotonic and absorption delaying agents and the like. As used herein, this term is particularly intended to include biocompatible implantable devices and encapsulated cell populations. The use of such media and agents for pharmaceutically active substances is well know in the art. Except insofar as any conventional media or agent is incompatible with the compositions of the present invention, its use in therapeutic compositions is contemplated. Supplementary active ingredients also can be incorporated into the compositions.

Under ordinary conditions of storage and use, the cell preparations may further contain a preservative to prevent growth of microorganisms. Intravenous vehicles include fluid and nutrient replenishers. Preservatives include antimicrobial agents, anti-oxidants, chelating agents and inert gases. The pH and exact concentration of the various components in the pharmaceutical are adjusted according to well-known parameters.

The compositions will advantageously be administered orally or by injection, including intravenously, intradermally, intraarterially, intraperitoneally, intracranially, intraarticularly, intraprostaticaly, intrapleurally, intramuscularly, subcutaneously, or by other method or any combination of the forgoing as would be known to one of ordinary skill in the art.

As will be recognized by those in the field, a "therapeutically effective amount" refers to an mount of such that, when provided to a subject in accordance with the disclosed and claimed methods effectsone of the following biological activities: treats type 2 diabetes; restores normoglycemia; reduces, suppresses, attenuates, or inhibits hyperglucogonemia or a condition associated with hyperglucogonemia; and reduces HbA1c; in a subject diagnosed with or otherwise having type 2 diabetes.

As understood in the art, such therapeutically effective amount will vary with many factors including the age and weight of the patient, the patient's physical condition, the condition to be treated, and other factors. An effective amount of the disclosed compounds will also vary with the particular combination administered. However, typical doses may contain from a lower limit of about 1 µg, 5 µg, 10 µg, 50 µg to 100 µg to an upper limit of about 100 µg, 500 µg, 1 mg, 5 mg, 10 mg, 50 mg or 100 mg of the pharmaceutical compound per day. Also contemplated are other dose ranges such as 0.1 µg to 1 mg of the compound per dose. The doses per day may be delivered in discrete unit doses, provided continuously in a 24 hour period or any portion of that the 24 hours. The number of doses per day may be from 1 to about 4 per day, although it could be more. Continuous delivery can be in the form of continuous infusions. The terms "QID," "TID," "BID" and "QD" refer to administration 4, 3, 2 and 1 times per day, respectively. Exemplary doses and infusion rates include from 0.005 nmol/kg to about 20 nmol/kg per discrete dose or from about 0.01/pmol/kg/min to about 10 pmol/kg/min in a continuous infusion. These doses and infusions can be delivered by intravenous administration (i.v.) or subcutaneous administration (s.c.). Exemplary total dose/delivery of the pharmaceutical composition given i.v. may be about 2 µg to about 8 mg per day, whereas total dose/delivery of the pharmaceutical composition given s.c. may be about 6 µg to about 6 mg per day.

The disclosed compounds may be administered, for example, at a daily dosage of, for example: from about 0.01 mg/kg to about 100 mg/kg; from about 0.01 mg/kg to about 80 mg/kg; from about 0.01 mg/kg to about 70 mg/kg; from about 0.01 mg/kg to about 60 mg/kg; from about 0.01 mg/kg to about 50 mg/kg; from about 0.01 mg/kg to about 40 mg/kg; from about 0.01 mg/kg to about 30 mg/kg; from about 0.01 mg/kg to about 25 mg/kg; from about 0.01 mg/kg to about 20 mg/kg; from about 0.01 mg/kg to about 15 mg/kg; from about 0.01 mg/kg to about 10 mg/kg; from about 0.01 mg/kg to about 5 mg/kg; from about 0.01 mg/kg to about 3 mg/kg; from about 0.01 mg/kg to about 1 mg/kg; from about 0.01 mg/kg to about 0.3 mg/kg from about 100 mg/kg to about 90 mg/kg; from about 100 mg/kg to about 80 mg/kg; from about 100 mg/kg to about 70 mg/kg; from about 100 mg/kg to about 60 mg/kg; from about 100 mg/kg to about 50 mg/kg; from about 100 mg/kg to about 40 mg/kg; from about 85 mg/kg to about 10 mg/kg; from about 75 mg/kg to about 20 mg/kg; from about 65 mg/kg to about 30 mg/kg; from about 55 mg/kg to about 35 mg/kg; or from about 55 mg/kg to about 45 mg/kg. Administration may be by injection of a single dose or in divided doses.

The term "unit dose" refers to a physically discrete unit suitable for use in a subject, each unit containing a predetermined quantity of the composition calculated to produce the desired response in association with its administration, i.e., the appropriate route and treatment regimen. The quantity to be administered, both according to number of treatments and unit dose, depends on the subject to be treated, the state of the subject, and the protection desired. Precise amounts of the therapeutic composition also depend on the judgment of the practitioner and are peculiar to each individual.

B. Insulin Therapy

In accordance with the present invention, it may prove advantageous to combine the methods disclosed herein with adjunct therapies or procedures to enhance the overall antidiabetic effect. Such therapies and procedures are set forth in general, below. A skilled physician will be apprised of the most appropriate fashion in which these therapies and procedures may be employed.

The present invention, though designed to eliminate the need for other therapies, is contemplated to provide advantageous use with traditional insulin supplementation, but at lower levels, such as below 90%, below 80%, below 70%, below 60%, below 50%, below 40%, below 30%, below 20%, below 15%, 10-15%, below 10%, 5-10%, below 5%, 4%, 3%, 2% or 1% of the normal daily dosage of insulin. The following are general guidelines for typical a "monotherapy" using insulin supplementation by injection, and can be applied here, albeit in the context of the aforementioned reductions in total daily dosage.

Insulin can be injected in the thighs, abdomen, upper arms or gluteal region. In children, the thighs or the abdomen are preferred. These offer a large area for frequent site rotation and are easily accessible for self-injection. Insulin injected in the abdomen is absorbed rapidly while from the thigh it is absorbed more slowly. Hence, patients should not switch from one area to the other at random. The abdomen should be used for the time of the day when a short interval between injection and meal is desired (usually pre-breakfast when the child may be in a hurry to go to school) and the thigh when the patient can wait 30 minutes after injection for his meal (usually pre-dinner). Within the selected area systematic site rotation must be practiced so that not more than one or two injections a month are given at any single spot. If site rotation is not practiced, fatty lumps known as lipohypertrophy may develop at frequently injected sites. These lumps are cosmetically unacceptable and, what is more important, insulin absorption from these regions is highly erratic.

Before injecting insulin, the selected site should be cleaned with alcohol. Injecting before the spirit evaporates can prove to be quite painful. The syringe is held like a pen in one hand, pinching up the skin between the thumb and index finger of the other hand, and inserting the needle through the skin at an angle of 45-90° to the surface. The piston is pushed down to inject insulin into the subcutaneous space (the space between the skin and muscle), then one waits for a few seconds after which release the pinched up skin before withdrawing the needle. The injection site should not be massaged.

For day-to-day management of diabetes, a combination of short acting and intermediate acting insulin is used. Some children in the first year after onset of diabetes may remain well controlled on a single injection of insulin each day. However, most diabetic children will require 2, 3 or even 4 shots of insulin a day for good control. A doctor should decide which regimen is best suited.

One injection regimen: A single injection comprising a mix of short acting and intermediate acting insulin (mixed in the same syringe) in 1:3 or 1:4 proportion is taken 20 to 30 minutes before breakfast. The usual total starting dose is 0.5 to 1.0 units/kg body weight per day. This regimen has three disadvantages: (1) all meals must be consumed at fixed times; (2) since the entire quantity of insulin is given at one time, a single large peak of insulin action is seen during the late and early evening hours making one prone to hyopglycemia at this time; (3) as the action of intermediate acting insulin rarely lasts beyond 16-18 hours, the patient's body remains underinsulinized during the early morning hours, the period during which insulin requirement in the body is actually the highest.

Two-injection regimen: This regimen is fairly popular. Two shots of insulin are taken—one before breakfast (⅔ of the total dose) and the other before dinner (⅓ of the total dose). Each is a combination of short acting and intermediate acting insulin in the ratio of 1:2 or 1:3 for the morning dose, and 1:2 or 1:1 for the evening dose. With this regimen the disadvantages of the single injection regimen are partly rectified. Some flexibility is possible for the evening meal. Further, as the total days' insulin is split, single large peaks of insulin action do not occur hence risk of hypoglycemia is reduced and one remains more or less evenly insulinized throughout the day. On this regimen, if the pre-breakfast blood glucose is high, while the 3 a.m. level is low, then the evening dose may need to be split so as to provide short acting insulin before dinner and intermediate acting insulin at bedtime.

Multi-dose insulin regimens: The body normally produces insulin in a basal-bolus manner, i.e., there is a constant basal secretion unrelated to meal intake and superimposed on this there is bolus insulin release in response to each meal. Multi-dose insulin regimens were devised to mimic this physiological pattern of insulin production. Short acting insulin is taken before each major meal (breakfast, lunch and dinner) to provide "bolus insulin" and intermediate acting insulin is administered once or twice a day for "basal insulin." Usually bolus insulin comprises 60% of the total dose and basal insulin makes up the remaining 40%. With this regimen you have a lot of flexibility. Both the timing as well as the quantity of each meal can be altered as desired by making appropriate alterations in the bolus insulin doses. To take maximum advantage of this regimen, one should learn "carbohydrate counting" and work out carbohydrate:insulin ratio—the number of grams of carbohydrate for which the body needs 1 unit of insulin.

C. Monitoring Glucose Levels

Any person suffering from diabetes will be very familiar with the need to regularly measure blood glucose levels. Blood glucose level is the amount of glucose, or sugar, in the blood. It is also is referred to as "serum glucose level." Normally, blood glucose levels stay within fairly narrow limits throughout the day (4 to 8 mmol/l), but are often higher after meals and usually lowest in the morning. Unfortunately, when a person has diabetes, their blood glucose level sometimes moves outside these limits. When one suffers from diabetes, it is important that glucose level be as near normal as possible. Stable blood glucose significantly reduces the risk of developing late-stage diabetic complications, which start to appear 10 to 15 years after diagnosis with type 1 diabetes, and often less than 10 years after diagnosis with type 2 diabetes.

Blood glucose levels can be measured very simply and quickly with a home blood glucose level testing kit, consisting of a measuring device itself and a test strip. To check blood glucose level, a small amount of blood is placed on the test strip, which is then placed into the device. After about 30 seconds, the device displays the blood glucose level. The best way to take a blood sample is by pricking the finger with a lancet. Ideal values are (a) 4 to 7 mmol/l before meals, (b) less than 10 mmol/l one-and-a-half hours after meals; and (c) around 8 mmol/l at bedtime.

People who have type 2 diabetes and are being treated with insulin should follow the schedule above. People who have type II diabetes and who are being treated with tablets or a special diet should measure their blood glucose levels once or twice a week, either before meals or one-and-a-half hours after a meal. They should also perform a 24-hour profile once or twice a month.

The main advantage for measuring blood glucose levels of insulin-treated diabetics in the morning is that adjusted amounts of insulin can be taken if the blood glucose level is high or low, thereby reducing the risk of developing late-stage diabetic complications. Similarly, the blood glucose level at bedtime should be between 7 and 10 mmol/l. If blood glucose is very low or very high at bedtime, there may be a need to adjust food intake or insulin dose. Blood glucose should also be measured any time the patient does not feel well, or thinks blood glucose is either too high or too low. People who have type 1 diabetes with a high level of glucose in their blood (more than 20 mmol/l), in addition to sugar traces in the urine, should check for ketone bodies in their urine, using a urine strip. If ketone bodies are present, it is a warning signal that they either have, or may develop, diabetic acidosis.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Previously, one of the following compounds discussed below have been studied in memapsin 2 inhibition (Ghosh et al., 2008), which the others are previously unpublished. Given the closely related substrate specificity for memapsin 1 and memapsin 2, the inventors chose to screen these previously identified memapsin 2 inhibitors for lead compounds as memapsin 1 inhibitors. Recombinant memapsin 1 ectodomain was prepared as described by Turner et al. (2002) and assayed using a commercially purchased fluorescent substrate. The compounds in Table 1 were found to be inhibitors of memapsin 1. The inhibition constants are also listed in Table 1. Activity of certain inhibitors was measured against Memapsin 2 which can be found in Table 2. Similarly, the Table 2 also shows the inhibition constants.

TABLE I

Inhibition of Memapsin 1

| Cpmd. No. | M1 inhibition Ki or IC$_{50}$ (nM) |
|---|---|
| 0113 | 0.0014 |
| 0213 | 1.005 |
| 0810 | 48 |
| 0910 | 6063 |
| 1910 | 46 |
| 1110 | 350 |
| 2710 | 53 |
| 1549 | 53 |
| 1589 | 70 |
| 0111 | 700 (IC$_{50}$) |
| 0211 | 37 |
| 0711 | 89 |
| 2211 | 500 (IC$_{50}$) |
| 2611 | 350 (IC$_{50}$) |
| 3511 | 11 |
| 4311 | 30 |

TABLE I-continued

Inhibition of Memapsin 1

| Cpmd. No. | M1 inhibition $K_i$ or $IC_{50}$ (nM) |
|---|---|
| 5211 | 521 |
| 5511 | 199 |
| 6212 | 63.1 |
| 6412 | 0.02 |
| 6512 | 76.6 |
| 6612 | 19.7 |
| 8234* | 137 |

*This compound was published in Ghosh et al. (2008) for inhibition vs. memapsin 2.

TABLE 2

Inhibition of Memapsin 2

| Cpmd. No. | M2 inhibition $K_i$ or $IC_{50}$ (nM) |
|---|---|
| 0113 | 563.5 |
| 0213 | 1657 |
| 6212 | 5812 |
| 6412 | 5245 |
| 6512 | 267 |
| 6612 | 6.56 |

Example 2

Inhibition of Tmem27 Processing by Memapsin 1 Inhibitor 0211 in MIN6 Cells

Since memapsin 1 is responsible for the processing of Tmem27, the inhibition of memapsin 1 inhibitor on the processing of Tmem27 in a pancreatic beta cell line was attempted. Cells of the pancreatic beta cell line MIN6 (Miyazaki et al., 1990; incorporated by reference herein) were grown in the presence of various inhibitors, lysed and then subjected to Western blot using a monoclonal antibody vs. Tmem27 C-terminal region. The results (FIG. 1) show that the 22-kDa C-terminal fragment of Tmem27 (lane 1) was reduced to less than 5% (lane 3) and completely abolished (lane 4) by 0.4 µM and 0.9 µM of inhibitor 0211, respectively. Compound J (Esterhazy et al., 2011; incorporated by reference herein) was used as positive control. C-terminal fragment of Tmem27 was preserved from degradation (lane 5) by the presence of gamma-secretase inhibitor DAPT in lanes 1-4. These results indicated that inhibitor 0211 penetrated MIN6 cells and effectively inhibited the processing of Tmem27 by memapsin 1.

Reduction of Plasma Glucose in ob/ob Mice by Memapsin 1 Inhibitors.

To demonstrate in vivo inhibition of memapsin 1 inhibitors, memapsin 1 inhibitors 8234 and 0211 were administered to ob/ob mice (Lindström P., 2007; incorporated by reference herein), which has high blood glucose and is a model animal for type 2 diabetes.

Experimental Procedures.

Four week old female B6.V-Lepob/J mice were ordered from The Jackson Laboratory (Bar Harbor. Me.). Group 8234 initially consisted of 2 control and 2 experimental mice. Group 0211 consisted of 4 control and 4 experimental mice. After acclimatization for one week to allow the mice to be familiar with the environment and handling, they were fasted 6 hour then 2 µl of whole blood was collected by saphenous vein bleeding (prebleed 1) and used to measure blood glucose with an AlphaTRAK 2 blood glucose monitoring system which gives blood glucose values in mg/dl. A conversion factor of 0.0555 was used to convert all values to mmol/l. Mice in the 328 group were bled in the same manner 10 days after prebleed 1 (prebleed 2) and blood glucose was measured. Blood was collected from mice in the 0211 group 3 days (prebleed 2) after prebleed 1 for blood glucose measurement. Two days after prebleed 2 for the 328 group or 6 days for the 0211 group, 2 µl of 6 hour fasting blood was collected by saphenous vein bleeding (day 1) and blood glucose was measured. Also on day 1 the mice were randomly assigned to receive intraperitoneal injections with either vehicle alone (PEG 300/D5W, 50/50, v/v) or a solution of one of the designed inhibitors at a dose of 30 mg/kg body weight. The concentration of the inhibitors for injection was 20 mg/ml and the volume injected varied from 0.04 ml to 0.06 ml depending on the daily weight of the mice.

Mice received daily intraperitoneal injections of inhibitor or vehicle until a reduction in three consistent blood glucose measurements had been observed (a minimum of 11 injections as in group 8234) or when a total of 14 injections had been made (as in group 0211). Blood glucose monitoring continued with blood collection every three to four days until the blood glucose levels converged with the controls or until a total of 24 blood samples were collected. Group 8234 had a total of 14 blood samples collected, 2 prebleed and 12 during and after treatment with inhibitor.

Figure 2:
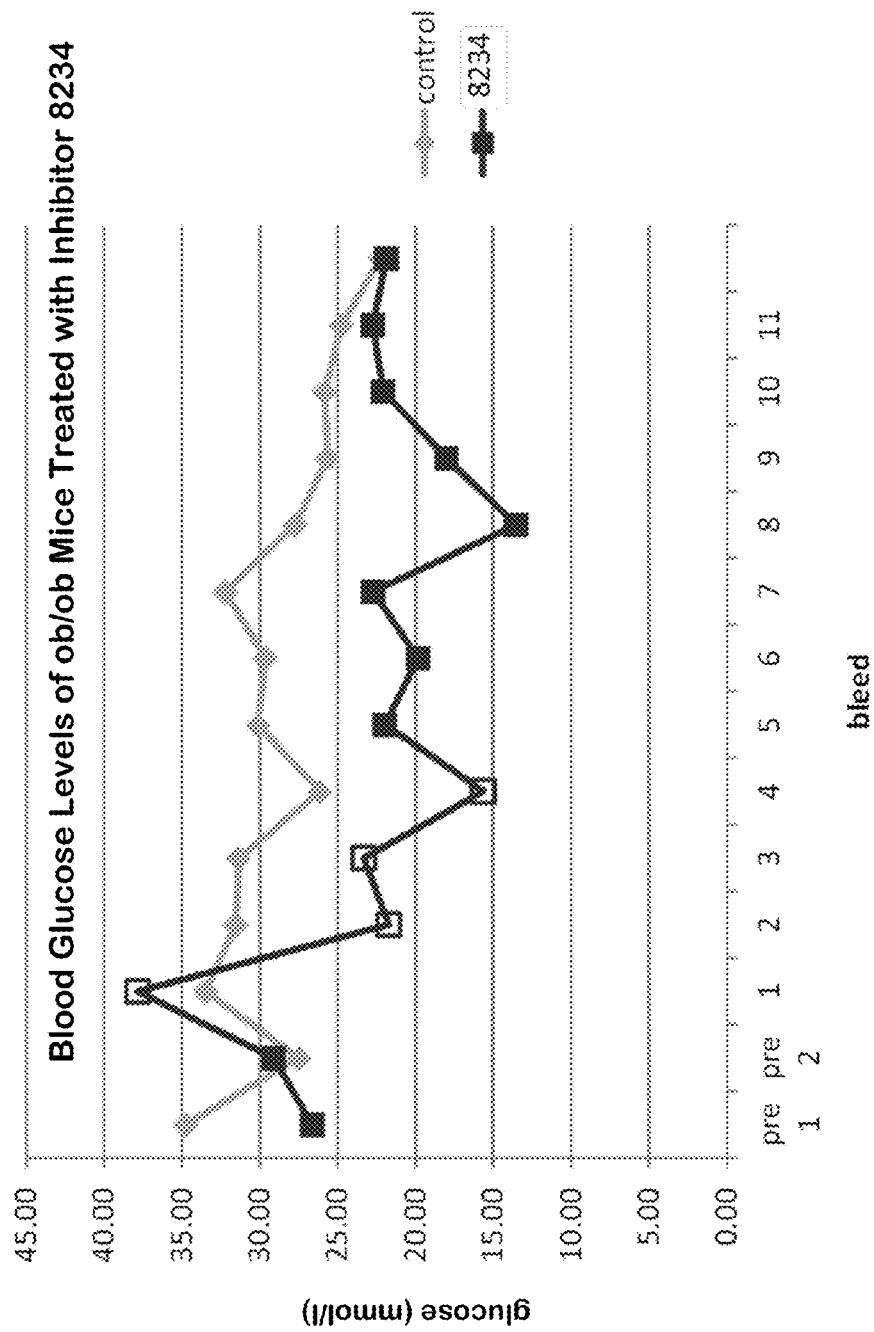
FIG. 2. Plasma glucose level of ob/ob mice treated with inhibitor 8234 (black) and the control group (light gray). The intervals of bleeds were 3 days. The injection of inhibitor were made at bleed number 1, 2, 3 and 4 as shown in open square data points.

Results.

the plasma glucose level of mice treated with inhibitor 8234 and the control is shown in FIG. 2. As can be seen in the FIG. 2, three days after the first inhibitor injection (at bleed 2), the glucose level in the experimental group dropped and remained below that of the control group through to the fourth injection (bleed 4) at that point the inhibitor injection stopped. The plasma glucose level of the experimental group remained below that of the control group through bleed 10 and merged at bleed 11.

Figure 3:
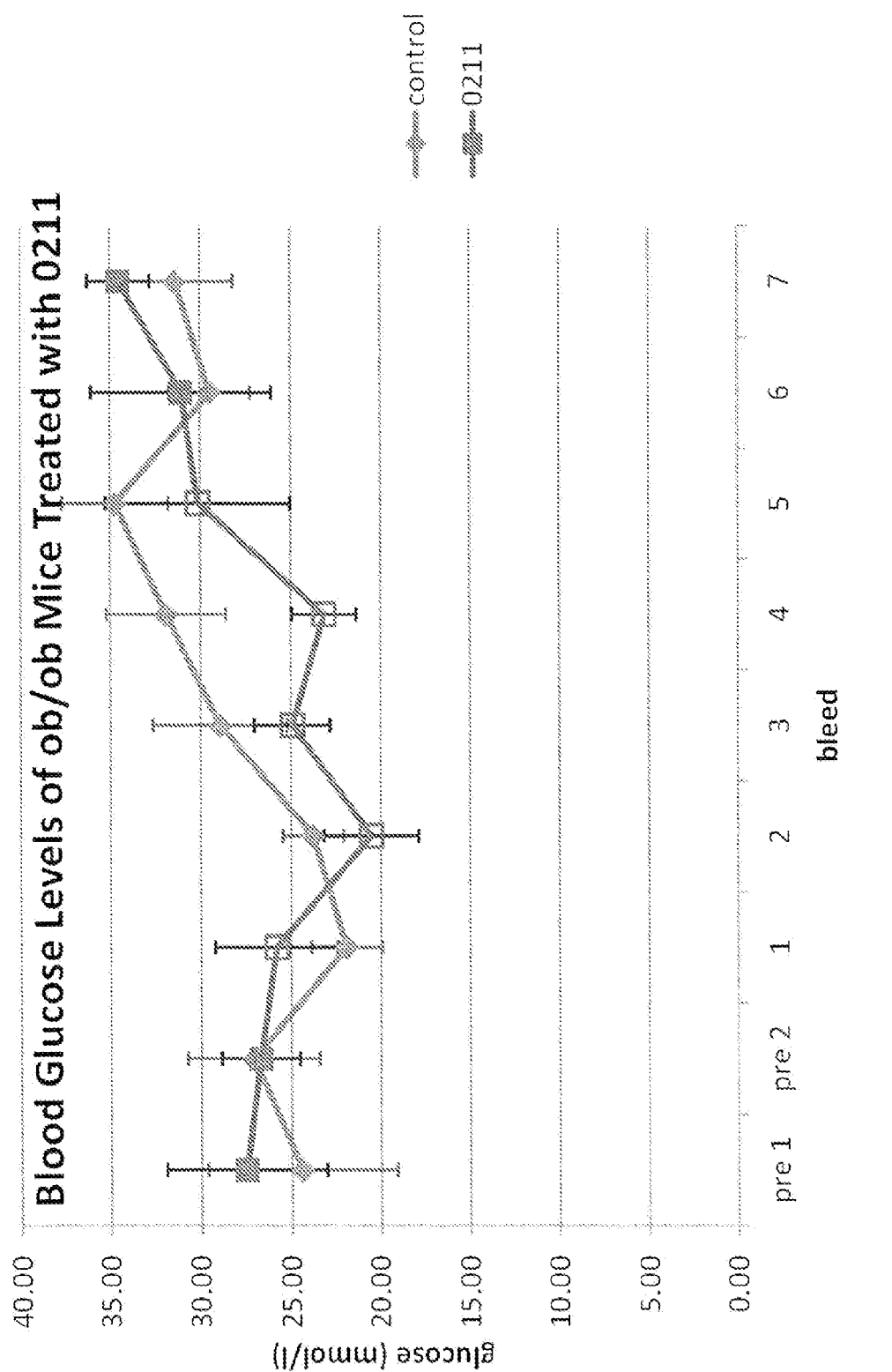
FIG. 3. Plasma glucose level of ob/ob mice treated with inhibitor 0211 (diamond, light gray) and the control group (square, dark gray). The inhibitor injections were made at 5 time points as shown in open square data points.

A similar comparison is shown in FIG. 3, which shows the plasma glucose level of ob/ob mice treated with inhibitor 0211 as compared with that of the control group. Similar to the results in FIG. 2, the plasma glucose level of the experimental group dropped below that of the control group 3 days after the first injection. The two groups merged 3 days after the stop of inhibitor injection (bleed 6).

Figure 4:
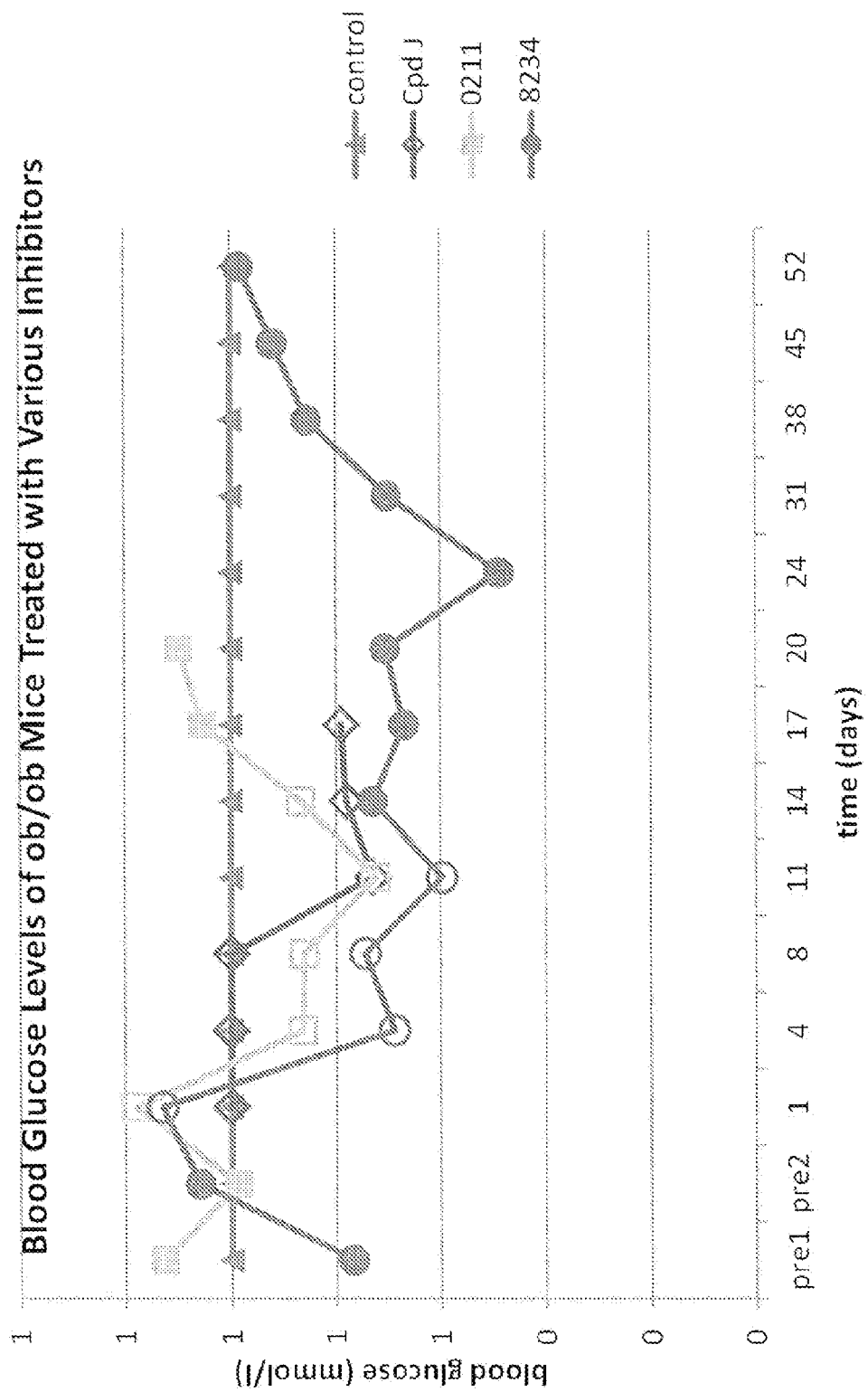
FIG. 4. Relative plasma glucose levels of ob/ob mice treated with inhibitors 8234 (circle), 0211 (sguare), and Compound J (Cpd J, triangles) as compared with controls (diamond) taken as 1.0. The data for Cpd J were taken from the paper of Esterhazy et al., 2011, which is incorporated by reference herein.

For a clearer comparison of the two experiments, the results in FIG. 2 and FIG. 3 are plotted in FIG. 4 in which the control data were taken as 1.0 in each data point. All three inhibitors reduced plasma glucose level to a similar extent. Inhibitor 8234 had a longer duration for its inhibition effect as the suppression of glucose level persisted over 21 days after the inhibition stopped.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VI. REFERENCES

The following references, to the extent that they provide exemplary procedural or other details supplementary to those set forth herein, are specifically incorporated herein by reference.

Akpinar, P., Kuwajima, S., Krutzfeldt, J., and Stoffel, M. (2005). Tmem27: a cleaved and shed plasma membrane protein that stimulates pancreatic beta cell proliferation. Cell Metab. 2, 385-397.

Altirriba, J., Gasa, R., Casas, S., Ramirez-Bajo, M. J., Ros, S., Gutierrez-Casas S, Casini P, Piquer S, Altirriba J, Soty M, Cadavez L, Gomis R, Novials A. (2010). BACE2 plays a role in the insulin receptor trafficking in pancreatic β-cells. Am J Physiol Endocrinol Metab. 299: E1087-1095.

Dalmau, A., Ruiz de VIIIa, M. C., Barbera, A., and Gomis, R. (2010). The role of transmembrane protein 27 (TMEM27) in islet physiology and its potential use as a beta cell mass biomarker. Diabetologia 53, 1406-1414.

Esterházy, D., Stützer, I., Wang, H. et al. (2011). Bace2 Is a Beta Cell-Enriched Protease that Regulates Pancreatic Beta Cell Function and Mass. *Cell Metab* 14, 365-377.

Fukui, K., Yang, Q., Cao, Y., Takahashi, N., Hatakeyama, H., Wang, H., Wada, J., Zhang, Y., Marselli, L., Nammo, T., et al. (2005). The HNF-1 target collectrin controls insulin exocytosis by SNARE complex formation. Cell Metab. 2, 373-384.

Ghosh A. K., Bilcer G., Harwood C. et al. (2001) Structure-based design: potent inhibitors of human brain memapsin 2 (b-secretase). J. Med. Chem. 44, 2865-2868.

Ghosh A. K., Devasamudramn T., Hong L., DeZutter C., Xu X., Weerasena V., Koelsch G., Bilcer G. and Tang J. (2005) Structure based design of cycloamide-urethane-derived novel inhibitors of human brain memapsin 2 (b-secretase). Bioorg. Med. Chem. Lett. 15, 15-20.

Ghosh A. K., Kumaragurubaran N., Hong L. et al. (2007) Design, synthesis, and X-ray structure of potent memapsin 2 (beta-secretase) inhibitors with isophthalamide derivatives as the P2-P3-ligands. J. Med. Chem. 50, 2399-2407.

Ghosh A. K., Kumaragurubaran N., Hong L. et al. (2008) Potent memapsin 2 (beta-secretase) inhibitors: design, synthesis, protein-ligand X ray structure, and in vivo evaluation. Bioorg. Med. Chem. Lett. 18, 1031-1036.

Hussain, I., Powell, D. J., Howlett, D. R., Chapman, G. A., Gilmour, L., Murdock, P. R., Tew, D. G., Meek, T. D., Chapman, C., Schneider, K. et al. (2000) ASP1 (BACE2) cleaves the amyloid precursor protein at the β-secretase site. *Mol. Cell Neurosci.* 16, 609-619.

Kahn S E, Zraika S, Utzschneider K M, Hull R L (2009) The beta cell lesion in type 2 diabetes: there has to be a primary functional abnormality. Diabetologia 52:1003-1012

Lin, X., Koelsch, G., Wu, S., Downs, D., Dashti, A., and Tang, J. (2000) Human aspartic protease memapsin 2 cleaves the betasecretase site of beta-amyloid precursor protein. Proc. Natl. Acad. Sci. U.S.A. 97, 1456-1460

Lidstrom, P. (2007) The physiology of obese-hyperglycemic mice [ob/ob mice]. ScientificWordJournal. 7, 666-85.

Miyazaki, J., Araki, K., Yamato, E., kengami, H., Asano, T., Shibasaki, Y., Oka, Y., Yamamura, K. (1990) Establishment of a pancreatic beta cell line that retains glucose-inducible insulin secretion: special reference to expression of glucose transporter isoforms. Endocrinology, 127, 126-32.

Ostermann, N. et al. (2006) Crystal structure of human BACE2 in complex with a hydroxyethylamine transition-state inhibitor. *J. Mol. Biol.* 355, 248-261.

Shih, D. Q., Screenan, S., Munoz, K. N., Philipson, L., Pontoglio, M., Yaniv, M., Polonsky, K. S., and Stoffel, M. (2001). Loss of HNF-1alpha function in mice leads to abnormal expression of genes involved in pancreatic islet development and metabolism. Diabetes 50, 2472-2480.

Turner, R. T., 3rd, Koelsch, G., Hong, L., Castanheira, P., Ermolieff, J., Ghosh, A. K., and Tang, J. (2001). Subsite specificity of memapsin 2 (beta-secretase): implications for inhibitor design. Biochemistry 40, 10001-10006.

Turner. R. T., 3rd, Loy, J. A., Nguyen, C., Devasamudram, T., Ghosh, A. K., Koelsch, G., and Tang, J. (2002). Specificity of memapsin 1 and its implications on the design of memapsin 2 (beta-secretase) inhibitor selectivity. Biochemistry 41, 8742-8746.

Vassar, R., Bennett, B. D., Babu-Khan, S., Kahn, S., Mendiaz, E. A., Denis, P., Teplow, D. B., Ross, S., Amarante, P., Loeloff, R. et al. (1999) β-Secretase cleavage of Alzheimer's amyloid precursor protein by the transmembrane aspartic protease BACE. Science 286, 735-741.

Wild, S., Roglic, G., Green, A., Sicree, R. & King, H. (2004) Global prevalence of diabetes: estimates for the year 2000 and projections for 2030. Diabetes Care 27, 1047-1053.

Yan, R., Bienkowski, M. J., Shuck, M. E., Miao, H., Tory, M. C., Pauley, A. M., Brashier, J. R., Stratman, N. C., Mathews, W. R., Buhl, A. E. et al. (1999) Membrane-anchored aspartyl protease with Alzheimer's disease β-secretase activity. *Nature* 402, 533-537.

What is claimed is:

1. A method of inhibiting memapsin 1 activity comprising contacting a memapsin 1 enzyme with a compound having a formula:

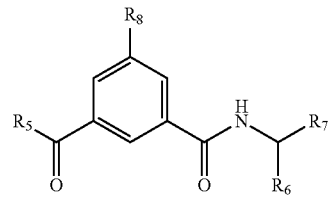

(III)

wherein $R_5$ is:

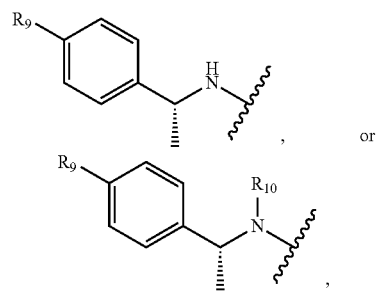

wherein:

$R_9$ is hydrogen or halo;

$R_{10}$ is alkyl$_{(C \leq 4)}$;

$R_6$ is hydrogen, alkyl$_{(C \leq 8)}$, aralkyl$_{(C \leq 8)}$, or a substituted version of the alkyl$_{(C \leq 8)}$ or aralkyl$_{(C \leq 8)}$ groups; or a halogen; and $R_7$ is:

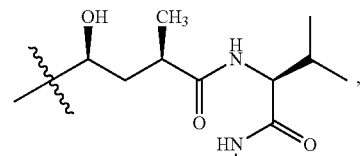

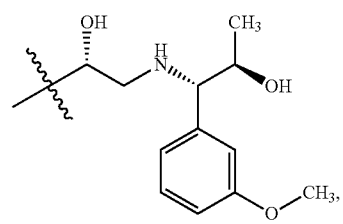

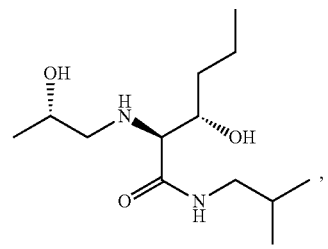

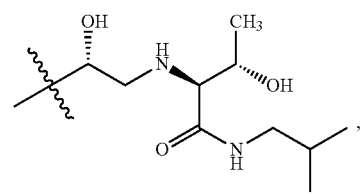

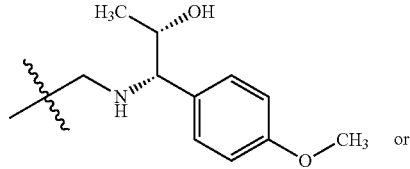 or

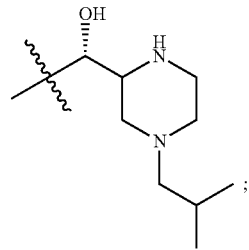

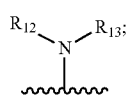

$R_8$ is hydrogen, alkyl$_{(C \leq 8)}$, or wherein: $R_{12}$ and $R_{13}$ are each independently hydrogen, alkyl$_{(C \leq 8)}$, or alkylsulfonyl$_{(C \leq 8)}$, wherein (i) if $R_9$ is hydrogen, then $R_8$ must be hydrogen or alkyl$_{(C \leq 8)}$, and (ii) if $R_8$ is

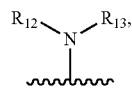

then $R_9$ must be halo, and one or both of $R_{12}$ and $R_{13}$ must be hydrogen, or a pharmaceutically acceptable salt or tautomer.

2. The method of claim 1, wherein the compound has formula III, wherein the formula is:

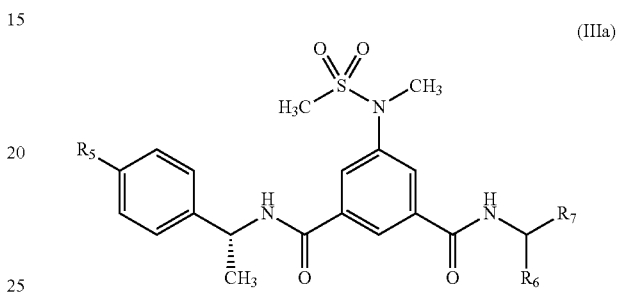

(IIIa)

wherein:

$R_9$ is hydrogen or halo;

$R_6$ is hydrogen, alkyl$_{(C \leq 8)}$, aralkyl$_{(C \leq 8)}$, or a substituted version of the alkyl$_{(C \leq 8)}$ or aralkyl$_{(C \leq 8)}$ groups; or a halogen; and $R_7$ is:

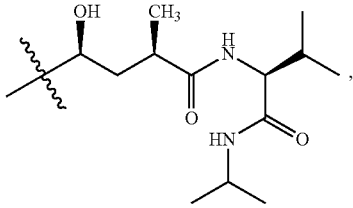

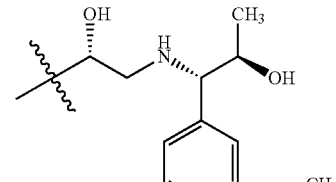

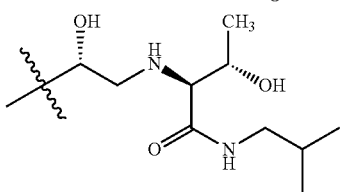

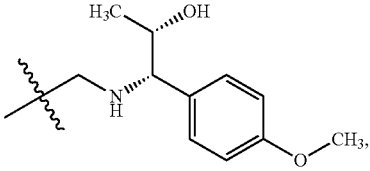

-continued

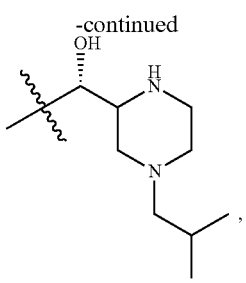

or a pharmaceutically acceptable salt or tautomer.

3. The method of claim 1, wherein the compound has formula III, wherein $R_5$ is

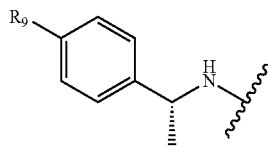

4. The method of claim 3, wherein $R_9$ is hydrogen.
5. The method of claim 3, wherein $R_9$ is halo.
6. The method of claim 3, wherein $R_{10}$ is methyl.
7. The method of claim 1, wherein the compound has formula III, wherein $R_6$ is benzyl or isobutyl.
8. The method of claim 1, wherein the compound has formula III, wherein $R_7$ is:

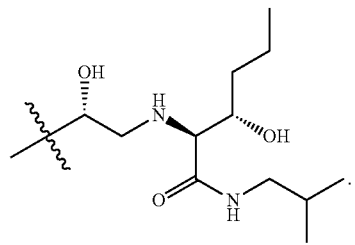 [SMILES: *[C@H](O)CN[C@H](C(=O)NCC(C)C)[C@@H](O)CCC]

9. The method of claim 1, wherein the compound has formula III, wherein $R_8$ is hydrogen.
10. The method of claim 1, wherein the compound has formula III, wherein $R_8$ is alkyl$_{(C\leq 8)}$.
11. The method of claim 1, wherein the compound has formula III, wherein $R_8$ is

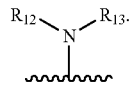

12. The method of claim 11, wherein one of $R_{12}$ and $R_{13}$ is alkyl$_{(C\leq 8)}$.
13. The method of claim 11, wherein one of $R_{12}$ and $R_{13}$ is methyl.
14. The method of claim 11, wherein one of $R_{12}$ and $R_{13}$ is alkylsulfonyl$_{(C\leq 8)}$.
15. The method of claim 14, wherein one of $R_{12}$ and $R_{13}$ is methylsulfonyl.
16. The method of claim 1, wherein the compound has formula III, wherein $R_9$ is iodo.

17. A method of treating a mammalian subject with type 2 diabetes comprising administering to said subject a compound having a formula:

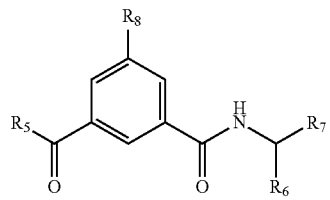

(III)

wherein $R_5$ is:

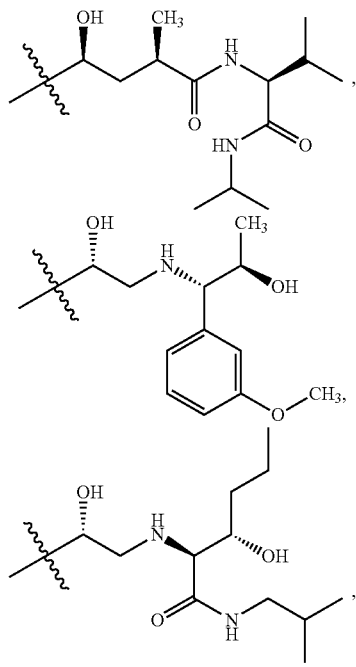

wherein:

$R_9$ is hydrogen or halo;

$R_{10}$ is alkyl$_{(C\leq 4)}$;

$R_6$ is hydrogen, alkyl$_{(C\leq 8)}$, aralkyl$_{(C\leq 8)}$, or a substituted version of the alkyl$_{(C\leq 8)}$ or aralkyl$_{(C\leq 8)}$ groups; or a halogen; and $R_7$ is:

-continued

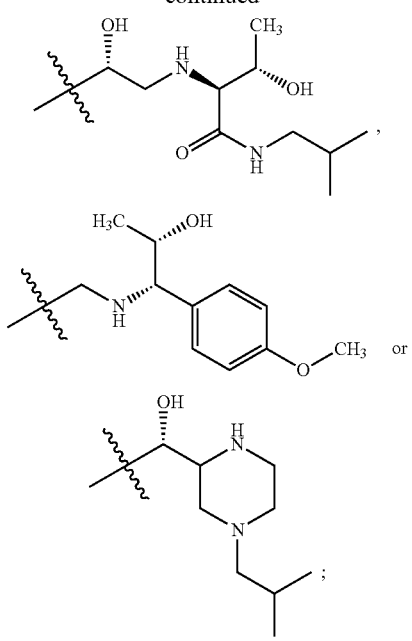

$R_8$ is hydrogen, alkyl$_{(C\leq 8)}$, or

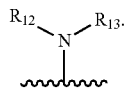

wherein: $R_{12}$ and $R_{13}$ are each independently hydrogen, alkyl$_{(C\leq 8)}$, or alkylsulfonyl$_{(C\leq 8)}$, wherein (i) if $R_9$ is hydrogen, then $R_8$ must be hydrogen or alkyl$_{(C\leq 8)}$, and (ii) if $R_8$ is

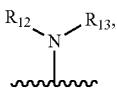

then $R_9$ must be halo, and one or both of $R_{12}$ and $R_{13}$ must be hydrogen, or a pharmaceutically acceptable salt or tautomer.

18. A method of increasing pancreatic beta cell mass in a mammalian subject comprising administering to said subject a compound having a formula:

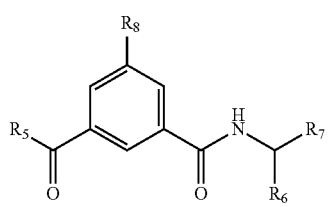

(III)

wherein $R_5$:

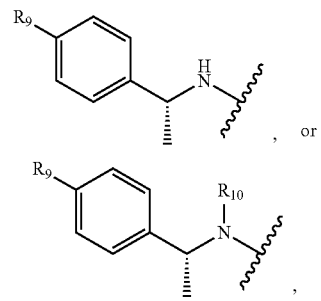

wherein:

$R_9$ is hydrogen or halo;

$R_{10}$ is alkyl$_{(C\leq 4)}$;

$R_6$ is hydrogen, alkyl$_{(C\leq 8)}$, aralkyl$_{(C\leq 8)}$, or a substituted version of the alkyl$_{(C\leq 8)}$ or aralkyl$_{(C\leq 8)}$ groups; or a halogen; and $R_7$ is:

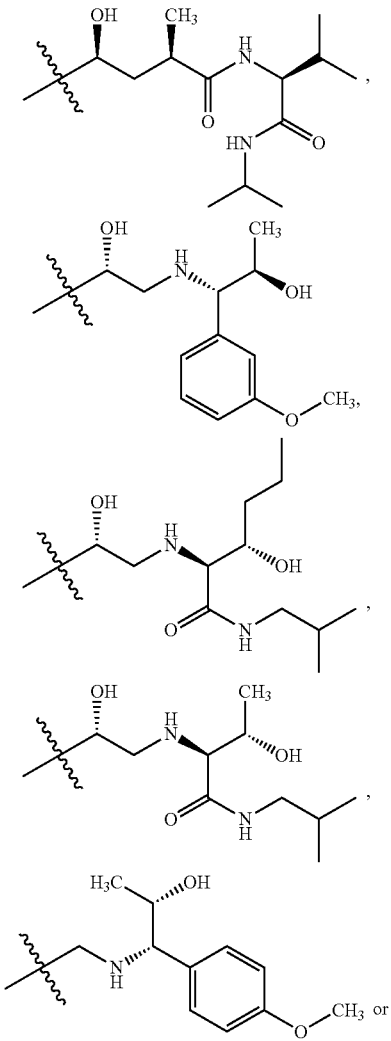

-continued
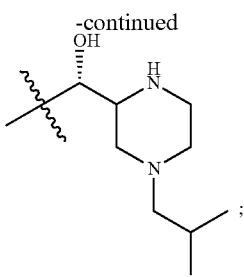
$R_8$ is hydrogen, alkyl$_{(C \leq 8)}$, or
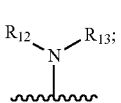
wherein: $R_{12}$ and $R_{13}$ are each independently hydrogen, alkyl$_{(C \leq 8)}$, or alkylsulfonyl$_{(C \leq 8)}$,
wherein (i) if $R_9$ is hydrogen, then $R_8$ must be hydrogen or alkyl$_{(C \leq 8)}$, and (ii) if $R_8$ is
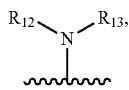
then $R_9$ must be halo, and one or both of $R_{12}$ and $R_{13}$ must be hydrogen,
or a pharmaceutically acceptable salt or tautomer.
* * * * *

UNITED STATES PATENT AND TRADEMARK OFFICE
CERTIFICATE OF CORRECTION

PATENT NO. : 9,096,541 B2  
APPLICATION NO. : 13/794031  
DATED : August 4, 2015  
INVENTOR(S) : Jordan Tang et al.

It is certified that error appears in the above-identified patent and that said Letters Patent is hereby corrected as shown below:

In the Claims

In claim 1, column 51, lines 20-29, delete the entire contents of lines 20-29 and insert

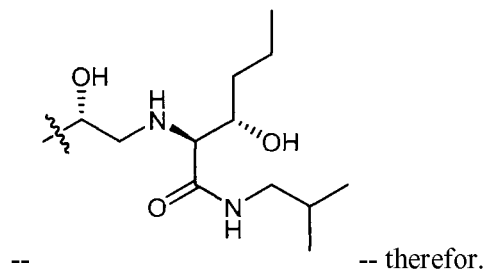

-- -- therefor.

In claim 1, column 51, lines 55-63, delete the entire contents of lines 55-63 and insert

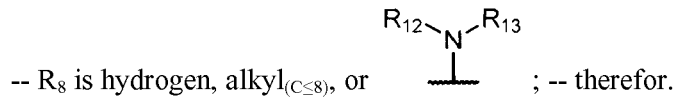

-- $R_8$ is hydrogen, alkyl$_{(C\leq 8)}$, or   ; -- therefor.

In claim 2, column 52, lines 15-25, delete the entire contents of lines 15-25 and insert

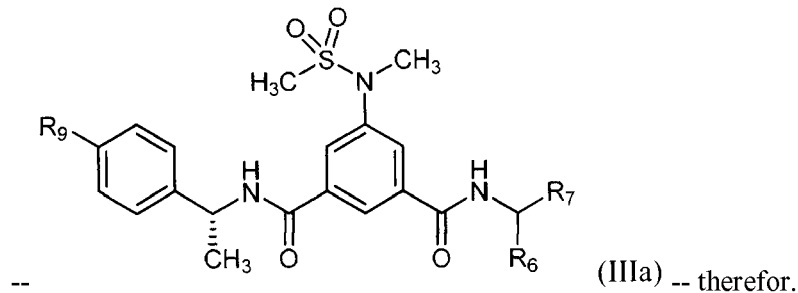

-- (IIIa) -- therefor.

Signed and Sealed this  
Twelfth Day of January, 2016

Michelle K. Lee  
*Director of the United States Patent and Trademark Office*

CERTIFICATE OF CORRECTION (continued)
U.S. Pat. No. 9,096,541 B2

In the Claims

In claim 3, column 53, lines 16-24, delete the entire contents of lines 16-24 and insert -- 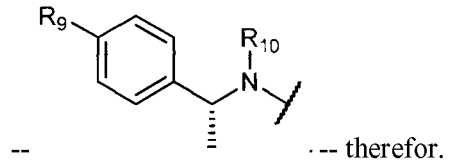 --- therefor.

In claim 17, column 55, lines 29-35, delete the entire contents of lines 29-35 and insert -- 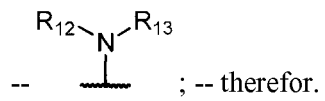 ; -- therefor.